(12) United States Patent
Saijo et al.

(10) Patent No.: US 9,963,482 B2
(45) Date of Patent: May 8, 2018

(54) PHOSPHATIDYLINOSITOL-3-KINASE INHIBITOR AND PHARMACEUTICAL COMPOSITION

(71) Applicant: Tohoku University, Miyagi (JP)

(72) Inventors: Ken Saijo, Miyagi (JP); Chikashi Ishioka, Miyagi (JP); Tadashi Katoh, Miyagi (JP)

(73) Assignee: Tohoku University, Miyagi (JP)

( * ) Notice: Subject to any disclaimer, the term of this patent is extended or adjusted under 35 U.S.C. 154(b) by 0 days. days.

(21) Appl. No.: 14/348,799

(22) PCT Filed: Sep. 25, 2012

(86) PCT No.: PCT/JP2012/074542
§ 371 (c)(1),
(2) Date: Mar. 31, 2014

(87) PCT Pub. No.: WO2013/047509
PCT Pub. Date: Apr. 4, 2013

(65) Prior Publication Data
US 2014/0235821 A1    Aug. 21, 2014

(30) Foreign Application Priority Data

Sep. 30, 2011    (JP) ................. 2011-217378

(51) Int. Cl.
| A61K 38/06 | (2006.01) |
| C07K 5/12 | (2006.01) |
| C07K 5/103 | (2006.01) |
| A61K 38/00 | (2006.01) |

(52) U.S. Cl.
CPC .............. *C07K 5/12* (2013.01); *A61K 38/06* (2013.01); *C07K 5/101* (2013.01); *C07K 5/123* (2013.01); *A61K 38/00* (2013.01)

(58) Field of Classification Search
None
See application file for complete search history.

(56) References Cited

U.S. PATENT DOCUMENTS

2010/0056435 A1* 3/2010 Ganesan et al. ............... 514/11

FOREIGN PATENT DOCUMENTS

| EP | 0 352 646 A2 | 1/1990 |
| JP | 2-85296 U | 7/1990 |
| JP | 4-79892 A | 3/1992 |
| JP | 2003-516418 A | 5/2003 |
| JP | 2008-542347 A | 11/2008 |
| JP | 2009-519224 A | 5/2009 |
| JP | 2010-510300 A | 4/2010 |
| WO | 01/42282 A1 | 6/2001 |
| WO | 2006/129105 A | 12/2006 |
| WO | WO2006129105 A1 * | 12/2006 |
| WO | 2007/061939 A2 | 5/2007 |
| WO | 2008/062201 A1 | 5/2008 |
| WO | 2009/141657 A1 | 11/2009 |
| WO | 2010/116173 A1 | 10/2010 |

OTHER PUBLICATIONS

Li, Khan W. et al, "Total synthesis of the antitumor depsipeptide fr-901,228." J. Am. Chem. Soc. (1996) 118(30) p. 7237-7238.*
Wang, Cheng et al, "Thailandepsins: bacterial products with potent histone deacetylase inhibitory activities and broad spectrum antiproliferative activities." J. Nat. Prod. (2011) 74 p. 2031-2038.*
The clinicaltrials.gov entry for the phase II clinical trial of FK228, https://clinicaltrials.gov/ct2/show/NCT00106301, identifier NCT00106301, available online Sep. 2008.*
Yurek-George, Alexander et al, "TOtal synthesis of spiruchostatin A, a potent histone deacetylase inhibitor." J. Am. Chem. Soc. (2004) 126 p. 1030-1031.*
International Search Report for corresponding International Application No. PCT/JP2012/074542, dated Nov. 20, 2012 (4 pages).
Fruman, D. et al.; "Phosphoinositide Kinases;" Annu. Rev. Boichem. 1998; pp. 481-507 (29 pages).
Cantley, L.; "The Phosphoinositide 3-Kinase Pathway;" Science AAAS; Science 296, 2002; pp. 1655-1657 (4 pages).
Samuels, Y. et al.; "High Frequency of Mutations of the PIK3CA Gene in Human Cancers;" Science; vol. 304; Apr. 23, 2004; p. 554 (1 page).
Ikenoue, T. et al.; "Functional Analysis of PIK3CA Gene Mutations in Human Colorectal Cancer;" Cancer Research AAKR; 2005; pp. 4562-4567 (7 pages).
Kang, S. et al.; "Phosphatidylinolitol 3-kinase mutations identified in human cancer are oncogenic;" PNAS; vol. 102, No. 3; Jan. 18, 2005; pp. 802-807 (6 pages).
Maehama, T. et al.; "The Tumor Suppressor, PTEN/MMACI, Dephosphorylates the Lipid Second Messenger, Phosphatidylinositol 3,4,5-Trisphosphate;" The Journal of Biological Chemistry Affinity Sites; 1998; pp. 13375-13378 (5 pages).
Salmena, L.; "Tenets of PTEN Tumor Suppression;" P.P. Cell 133; May 2, 2008; pp. 403-414 (12 pages).
Han, S. et al.; "Functional Evaluation of PTEN Missense Mutations Using in Vitro Phosphoinositide Phosphatase Assay;" Cancer Research 60; 2000; pp. 3147-3151 (6 pages).
Kong, D. et al.; "Advances in Development of Phosphatidylinositol 3-Kinase Inhibitors;" Curren Medicinal Chemistry 16; 2009; pp. 2839-2854 (16 pages).
Carew, J.; "Histone deacetylase inhibitors: Mechanisms of cell death and promise in combination cancer therapy;" Letters 269; Mar. 25, 2008; pp. 7-17 (11 pages).
Ueda, H. et al.; "The Journal of Antiobiotics;" vol. 47, No. 3; Ibaraki, Japan; pp. 301-310 (10 pages), 1994.
Furumai, R. et al.; "FK228 (Depsipeptide as a Natural Prodrug That Inhibits Class 1 Histone Deacetylases;" Cancer Research 62; 2002; pp. 4916-4921 (7 pages).
Wozniak, M.; "Vorinostat interferes with the signaling transduction pathway of T-cell receptor and synergizes with phosphoinositide-3 kinase inhibitors in cutaneous T-cell lymphoma;" Haematologica 95; 2010; pp. 613-621 (9 pages).

(Continued)

*Primary Examiner* — Fred H Reynolds
(74) *Attorney, Agent, or Firm* — Osha Liang LLP

(57) ABSTRACT

A substance contains a phosphatidylinositol-3-kinase (PI3K) inhibitor including a depsipeptide-class compound represented by formula (1), or a physiologically acceptable salt thereof that combines a PI3K inhibitory effect and an HDAC inhibitory effect to provide an anti-cancer pharmaceutical composition for the treatment of an intractable cancer.

6 Claims, 23 Drawing Sheets

(56) References Cited

OTHER PUBLICATIONS

Hanker, A.; "Romidepsin inhibits Ras-dependent growth transformation of NIH 3T3 fibroblasts and RIE-I epithelial cells independently of Ras signaling inhibition;" Journal of Molecular Signaling; Aug. 16, 2009; pp. 1-13 (13 pages).

Graham, C. et al.; "Evaluation of the Antitumor Efficacy, Pharmacokinetics, and Pharmacodynamics of the Histone Deacetylase Inhibitor Depsipeptide in Childhood Cancer Models In vivo;" Clinical Cancer Research AACR; 2006; 223-234 (13 pages).

Chen, C., et al.; "Mechanisms of Signal Transduction: Histone Acetylation-independent Effect of Histone Deacetylase Inhibitors on Akt through the Reshuffling of Protein Phosphatase 1 Complexes;" The Journal of Biological Chemistry Affinity Sites; vol. 280, No. 46; Nov. 18, 2005; pp. 38879-38887 (10 pages).

Kodani, M., et al.; "Supression of phosphatidylinositol 3-kinase/Akt signaling pathway is determinant of the sensitivity to a novel histone deacetylase inhibitor, FK228, in lung adenocarcinoma cells;" Oncology Reports 13; Yonago, Japan; 2005; pp. 477-483 (7 pages).

Tugendreich, S., et al.; "A Streamlined Process to Phenotypically Profile Heterologous cDNAs in Parallel Using Yeast Cell-Based Assays;" Genome Research; 2001; pp. 1899-1912 (15 pages).

Rodriguez-Escudero, I., et al.; "Reconstitution of the Mammalian P13K/PTEN/Akt pathway in yeast;" Biochemical Society; 2005; pp. 613-623 (11 pages).

Cid, V., et al.; "Assessment of PTEN tumor suppressor activity in nonmammalian models: the year of the yeast;" Oncogene; 2008; pp. 5431-5442 (12 pages).

Saijo, K., et al.; "Search for novel PI3K inhibitor by using budding yeast as screening tool;" Tohoko University; Series No. P10-5; May 31, 2011 (2 pages).

Narita, K., et al.; "Total Synthesis of the Bicyclic Depsipeptide HDAC Inhibitors Spiruchostatins A and B, 5″-epi-Spiruchostatin B, FK228 (FR0901228) and Preliminary Evaluation of their Biological Activity;" Chemistry a European Journal; 2009; pp. 11174-11186 (13 pages).

Takizawa, T., et al.; "Total synthesis of spiruchostatin B, a potent histone deacetylase inhibitor, from microorganism;" ChemComm; 2008; pp. 1677-1679 (3 pages).

Takizawa, T., et al.; "Total Synthesis of Spiruchostatin A—A Potent Histone Deacetylase Inhibitor;" Heterocycles, vol. 76, No. 1; 2008; pp. 275-290 (16 pages).

Rogers, B., et al.; "The Pleitropic Drug ABC Transporters from *Saccharomyces cerevisiae*;" J. Mol. Microbiol. Biotechnol. 3; 2001; pp. 207-214 (8 pages).

Alani, E., et al.; "A Method for Gene Disruption That Allows Repeated Use of URA3 Selection in the Construction of Multiply Disrupted Yeast Strains;" The Genetics Society of America; 1987; pp. 541-545 (5 pages).

Walker, E., et al.; "Structural Determinants of Phosphoinositide 3-Kinase Inhibition by Wortmannin, LY294002, Quercetin, Myricetin, and Staurosporine;" Molecular Cell, vol. 6; pp. 909-919; Oct. 2000 (11 pages).

Grünwald, V., et al.; "Inhibitors of mTOR Reverse Doxorubicin Resistance Conferred by PTEN Status in Prostate Cancer Cells;" Cancer Research AACR; 2002; pp. 6141-6145 (6 pages).

Ropero, S., et al.; "A truncating mutation of HDAC2 in human cancers confers resistance to histone deacetylase inhibition;" Nature Genetics; vol. 38, No. 5; May 2006; pp. 566-569 (4 pages).

Hanigan, C., et al.; "An Inactivating Mutation in HDAC2 Leads to Dysregulation of Apoptosis Mediated by APAF1;" Gastroenterology; 2008 pp. 1654-1664 (13 pages).

Ree, A., et al.; "HDAC2 deficiency and histone acetylation;" Nature Genetics; vol. 40, No. 7; Jul. 2008; pp. 812-813 (2 pages).

Xu, W., et al.; "Histone deacetylase inhibitors: molecular mechanisms of action;" Oncogene; 2007; pp. 5541-5552 (12 pages).

Richon, V., et al.; "Histone deacetylase inhibitor selectively induces p21WAF1 expression and gene-associated histone acetylation;" PNAS; vol. 97, No. 18; Aug. 29, 2000; pp. 10014-10019 (6 pages).

Nakajima, H., et al.; "FR901228, a Potent Antitumor Antibiotic, is a Novel Histone Deacetylase Inhibitor;" Experimental Cell Research 241; 1998; pp. 126-133 (8 pages).

Kumagai, T.; "Histone deacetylase inhibitor, suberoyalinide hydroxamic acid (Vorinostat, SAHA) profoundly inhibits the growth of human pancreatic cancer cells;" International Journal of Cancer 121; 2007; pp. 656-665 (10 pages).

Hirokawa, Y., et al.; "Signal Therapy of NF1-Deficient Tumor Xenograft in Mice by the Anti-PAK1 Drug FK228;" Cancer Biology & Therapy; vol. 4, No. 4; 2005; pp. 379-381 (3 pages).

Maruta, H., et al.; "Genome and familial tumor, Signal therapy of Neurofibromatosis;" Genomic Medicine; vol. 4, No. 2; 2004; pp. 185-192 (21 pages).

Wang, C., et al.; "Thailandepsins: Bacterial Products with Potent Histone Deacetylase Inhibitory Activities and Broad-Spectrum Antiproliferative Activities;" Journal of Natural Products; pp. 2031-2038 (8 pages) Retrieved from the internet: <http://pubs.acs.org/doi/abs/10.1021/np200324x/>, 2011 vol. 74 p. 2031-2038.

Kodani, M. et al.; "Synergy with amrubicin and Akt inhibitory effect of FK228 (FR091228) in lung adenocarcinoma cell line;" The Japan Lung Cancer Society; vol. 43, No. 5; 2003; pp. 581; P-389 (2 pages).

EPO Communication dated Sep. 25, 2015, with an Extended European Search Report, issued by the European Patent Office in related European Patent Application No. 12835791.0 [16 pages]. [Note: All references cited in this EESR were previously cited and submitted to the USPTO in the IDS filed on Jul. 21, 2015, and therefore, have not been recited or resubmitted herein.].

EPO Communication pursuant to Rule 164(1) EPC dated Jun. 9, 2015, with a Partial Supplementary European Search Report dated May 29, 2015, issued by the European Patent Office in corresponding European Application No. EP-12835791.0 (8 pages).

Harrison, Simon James, et al., "High Response Rates with the Combination of Bortezomib, Dexamethasone and the Pan-Histone Deacetylase Inhibitor Romidepsin in Patients with Relapsed or Refractory Multiple Myeloma in a Phase I/II Clinical Trial"; Blood: Ash Annual Meeting Abstracts, American Society of Hematology, U.S.; Jan. 1, 2008; XP002664394, ISSN: 0006-4971; pp. 1-2.

Niesvizky, M.D., Ruben, et al., "Phase 2 Trial of the Histone Deacetylase Inhibitor Romidepsin for the Treatment of Refractory Multiple Myeloma"; Cancer, vol. 117, No. 2, Sep. 22, 2010; XP055191447, ISSN: 0008-543X, DOI: 10.1002/cncr.25584; pp. 336-342.

Piekarz, Richard L., et al., "Phase II Multi-Institutional Trial of the Histone Deacetylase Inhibitor Romidepsin As Monotherapy for Patients With Cutaneous T-Cell Lymphoma"; Journal of Clinical Oncology, vol. 27, No. 32, Oct. 13, 2009; XP055191450, ISSN: 0732-183X, DOI: 10.1200/JCO.2008.21.6150; pp. 5410-5417.

Molife, L. R., et al., "Phase II, two-stage, single-arm trial of the histone deacetylase inhibitor (HDACi) romidepsin in metastatic castration-resistant prostate cancer (CRPC)"; Annals of Oncology, vol. 21, No. 1, Jul. 16, 2009; XP055191214, ISSN: 0923-7534, DOI: 10.1093/annonc/mdp270; pp. 109-113.

Sandor, Victor, et al., "Phase I Trial of the Histone Deacetylase Inhibitor, Depsipeptide (FR901228, NSC 630176), in Patients with Refractory Neoplasms"; Clinical Cancer Research, The American Association for Cancer Research, U.S., vol. 8, No. 3, Mar. 1, 2002; XP009012362, ISSN: 1078-0432; pp. 718-728.

* cited by examiner

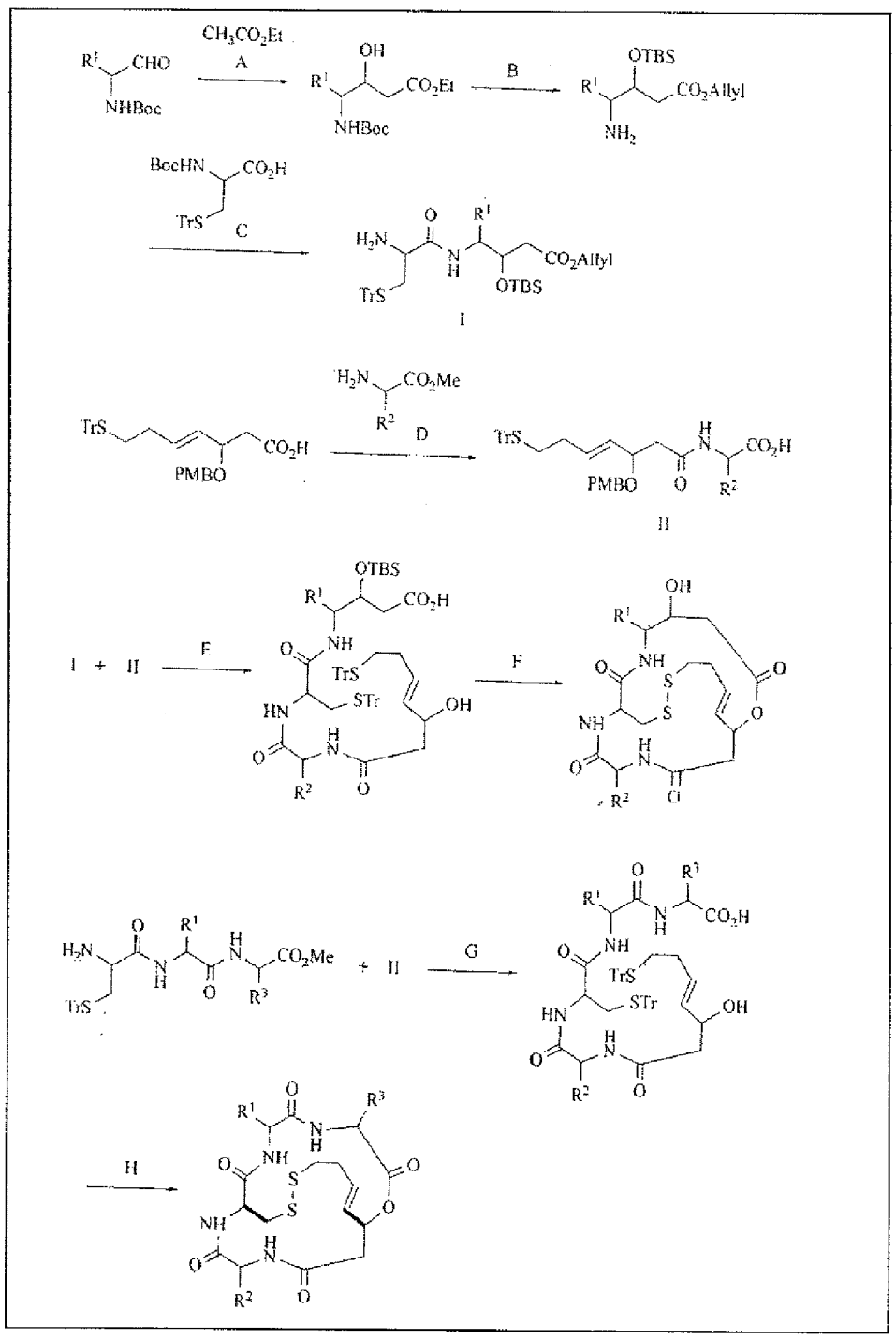
[Fig. 1]

[Fig. 2A]
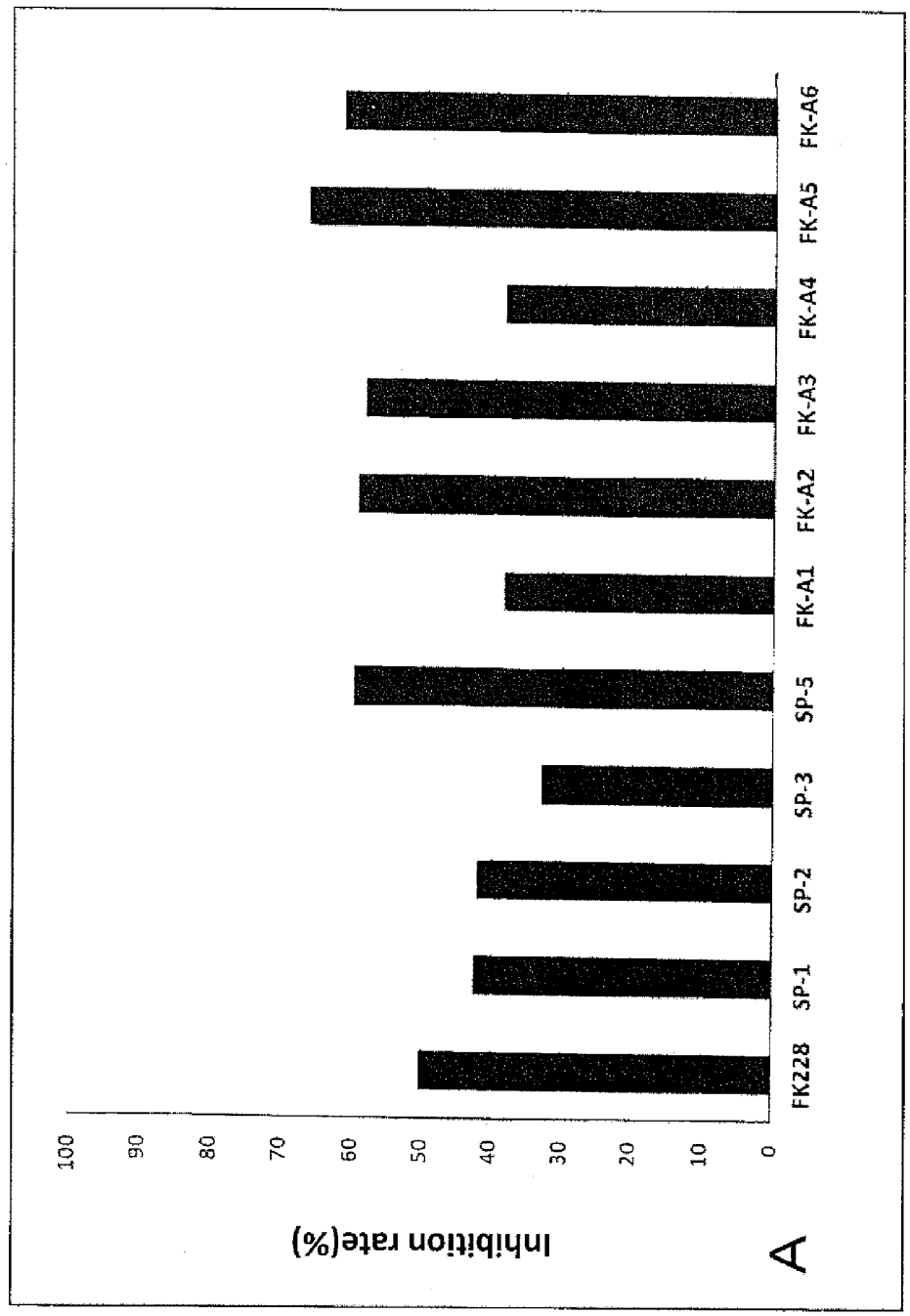

【Fig. 2B】
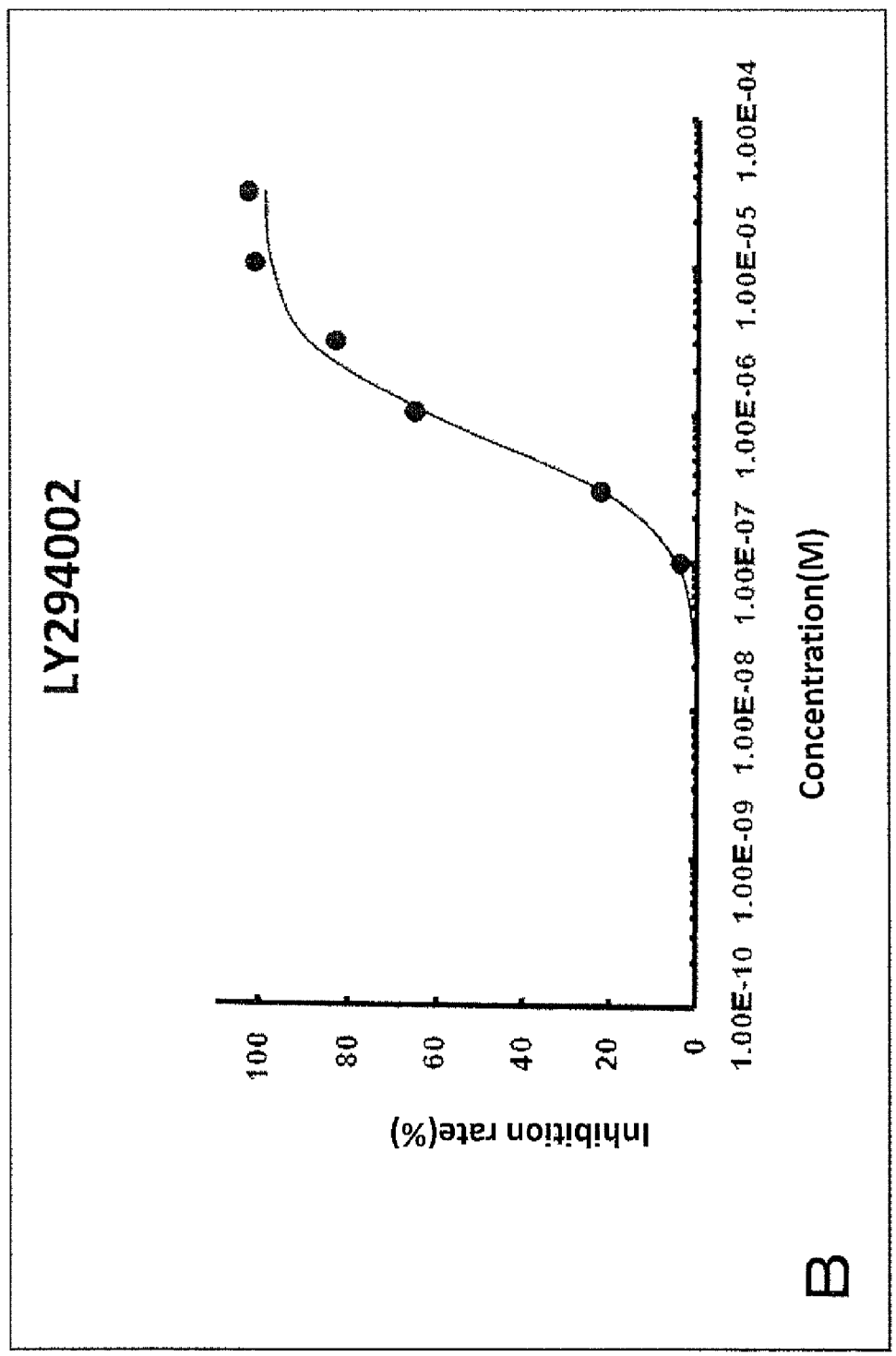

[Fig. 2C]
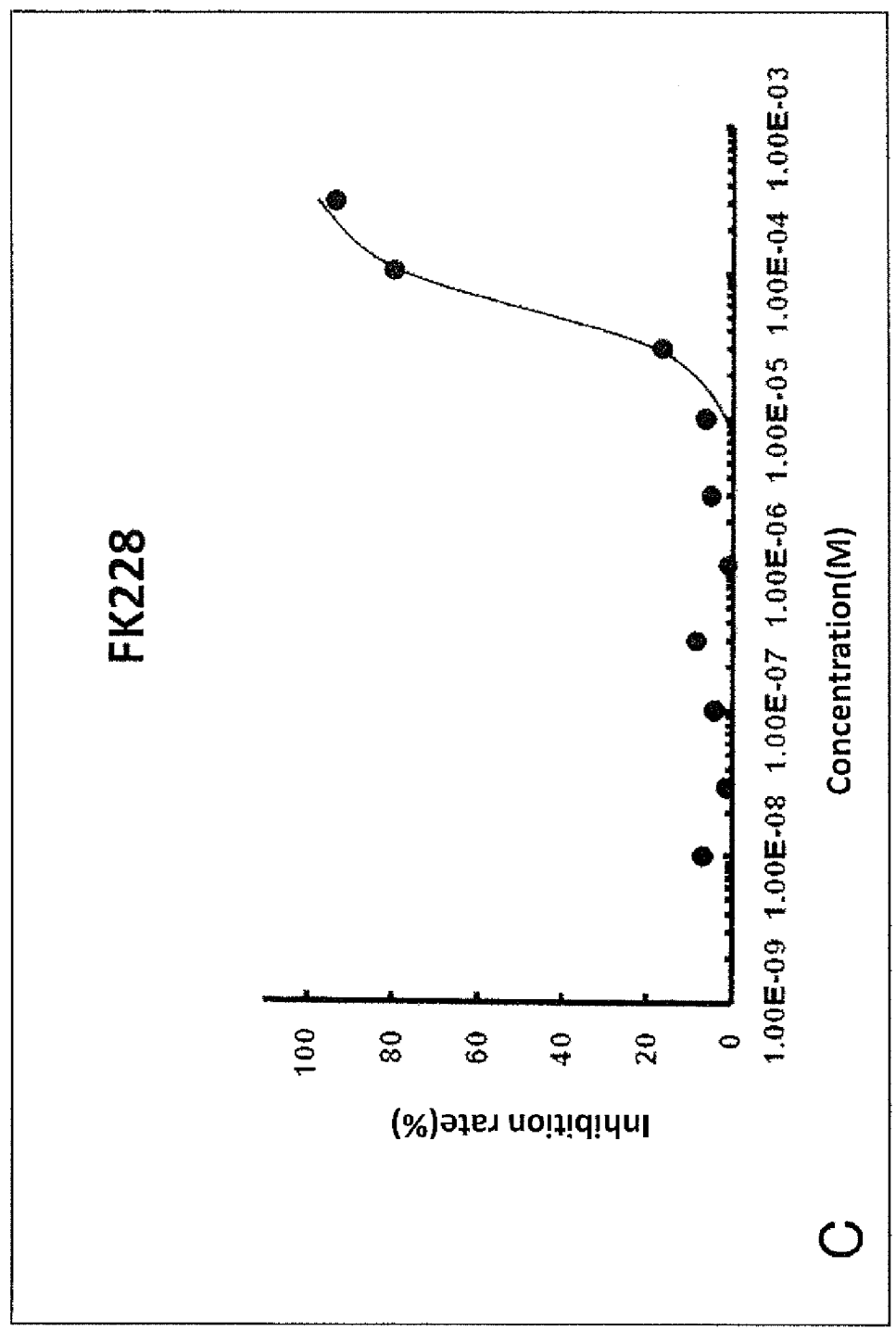

[Fig. 2D]
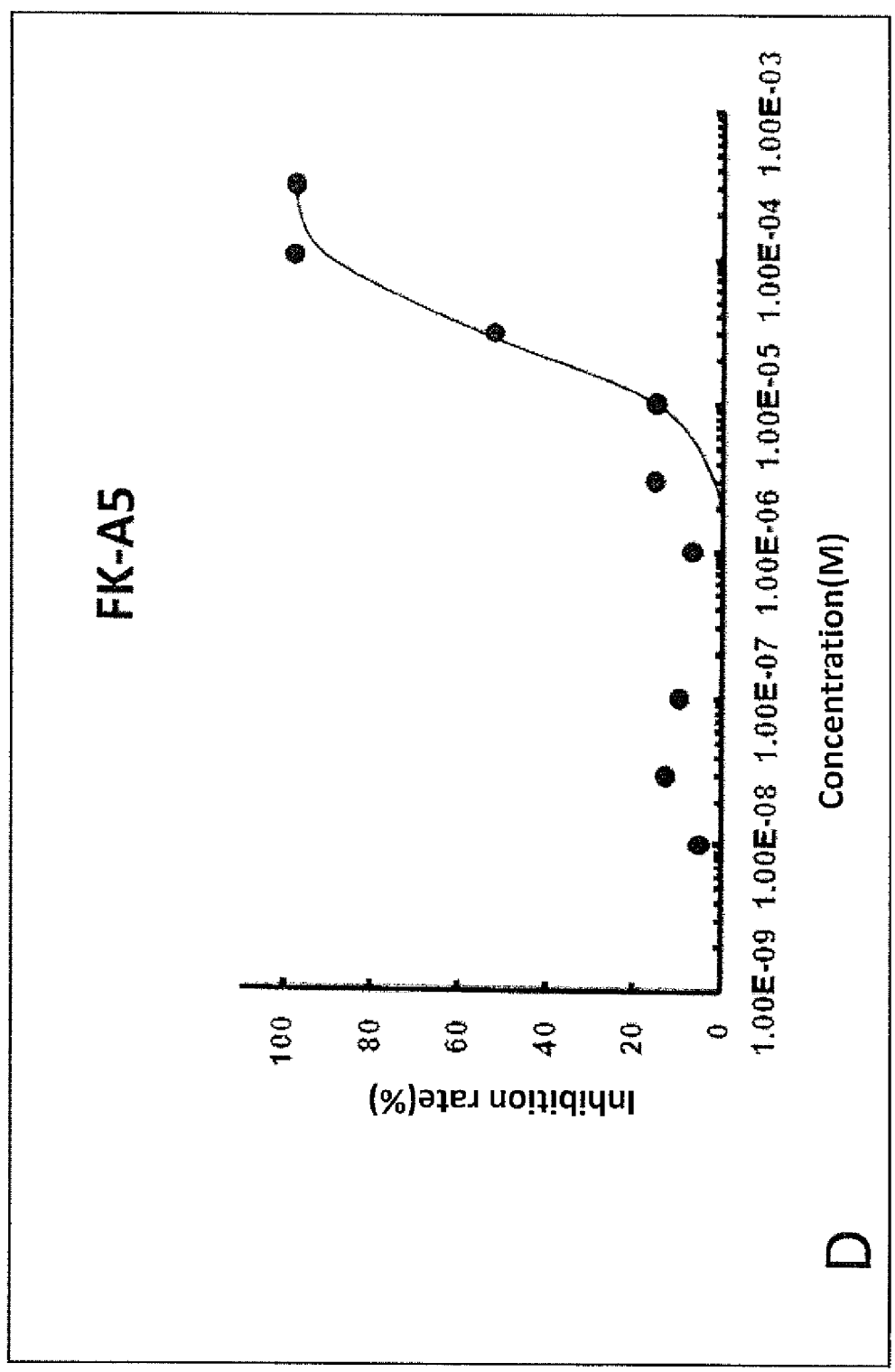

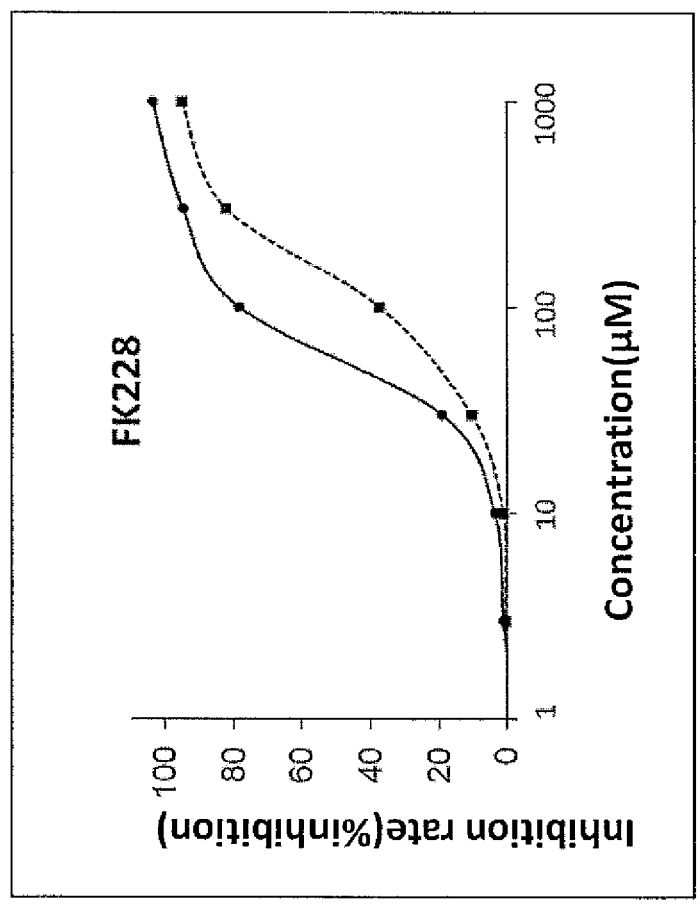
[Fig. 2E]

[Fig. 3]
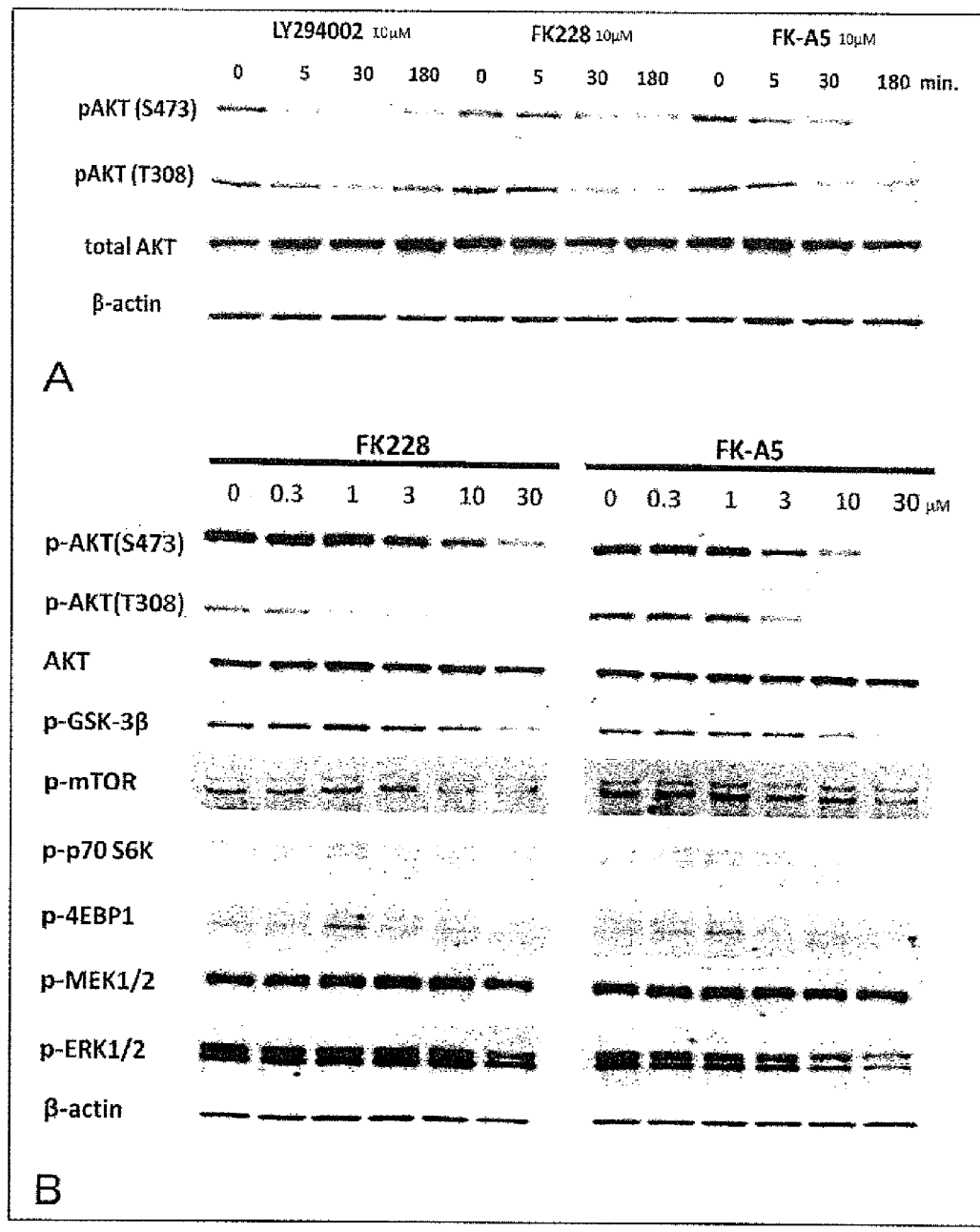

[Fig. 4A]
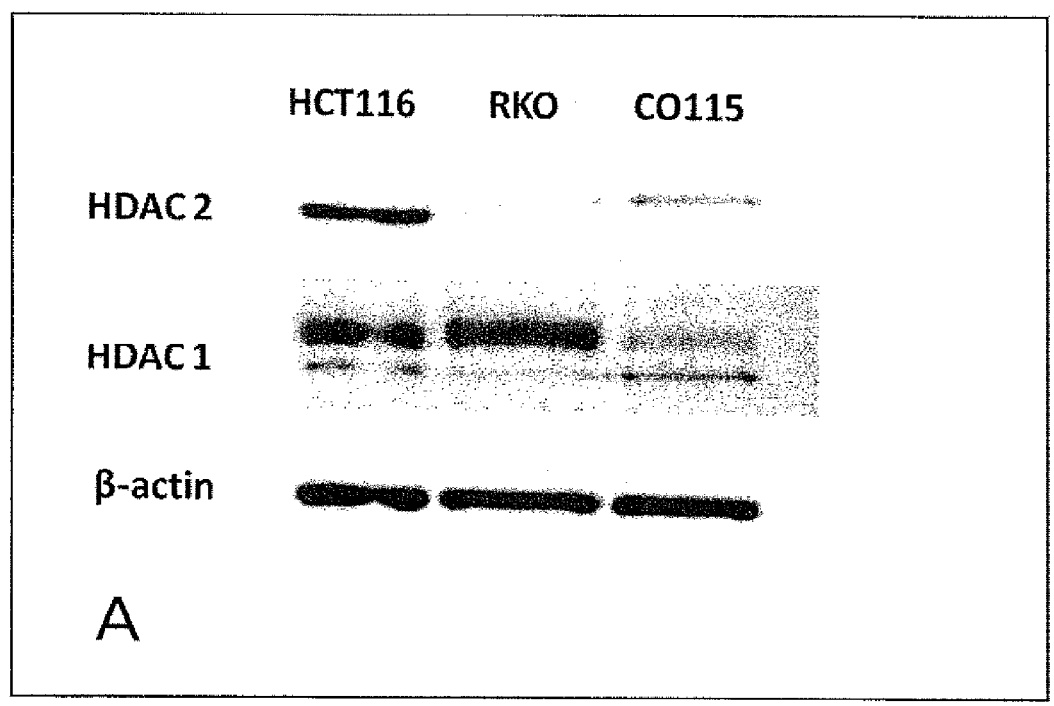

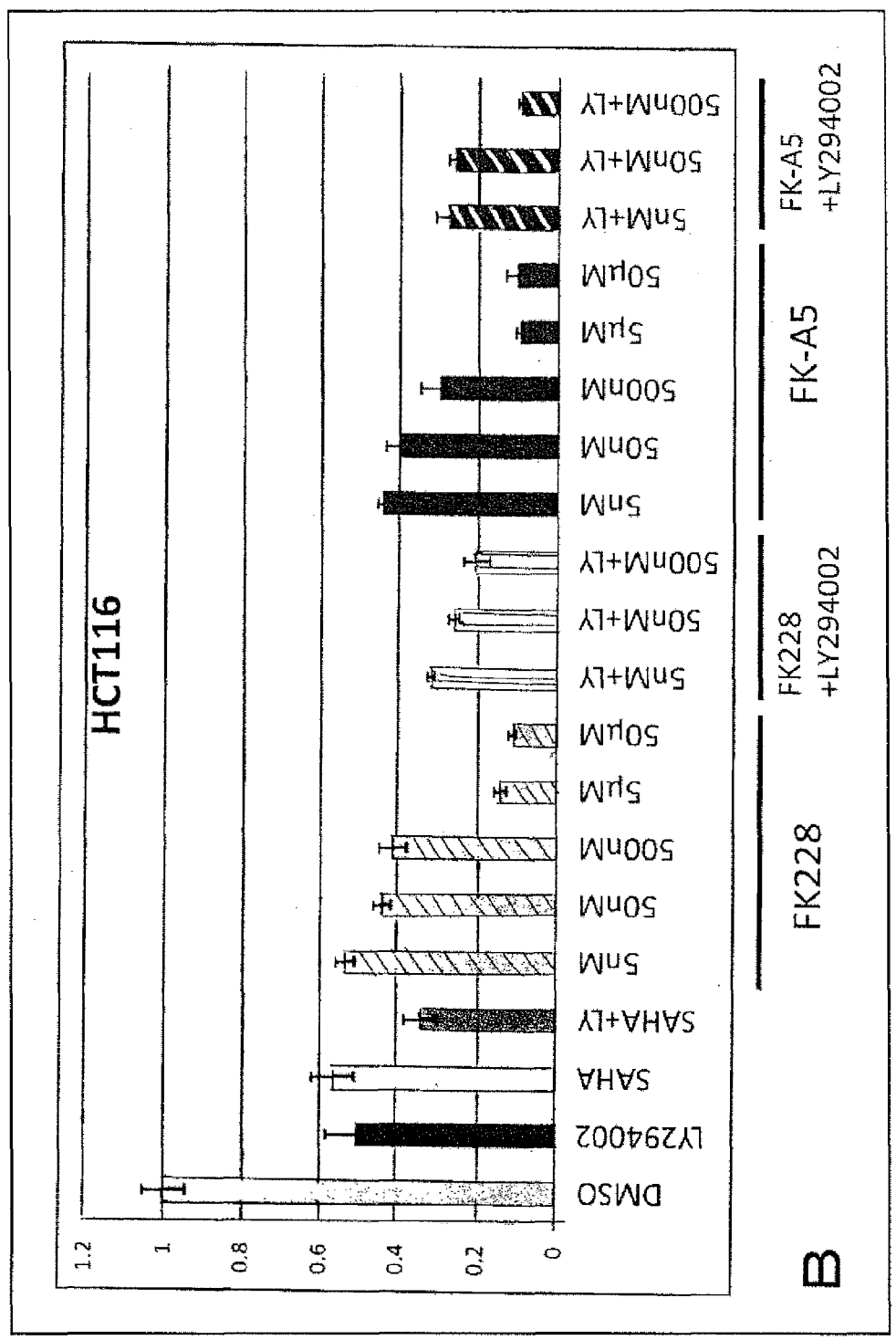
[Fig. 4B]

[Fig. 4C]
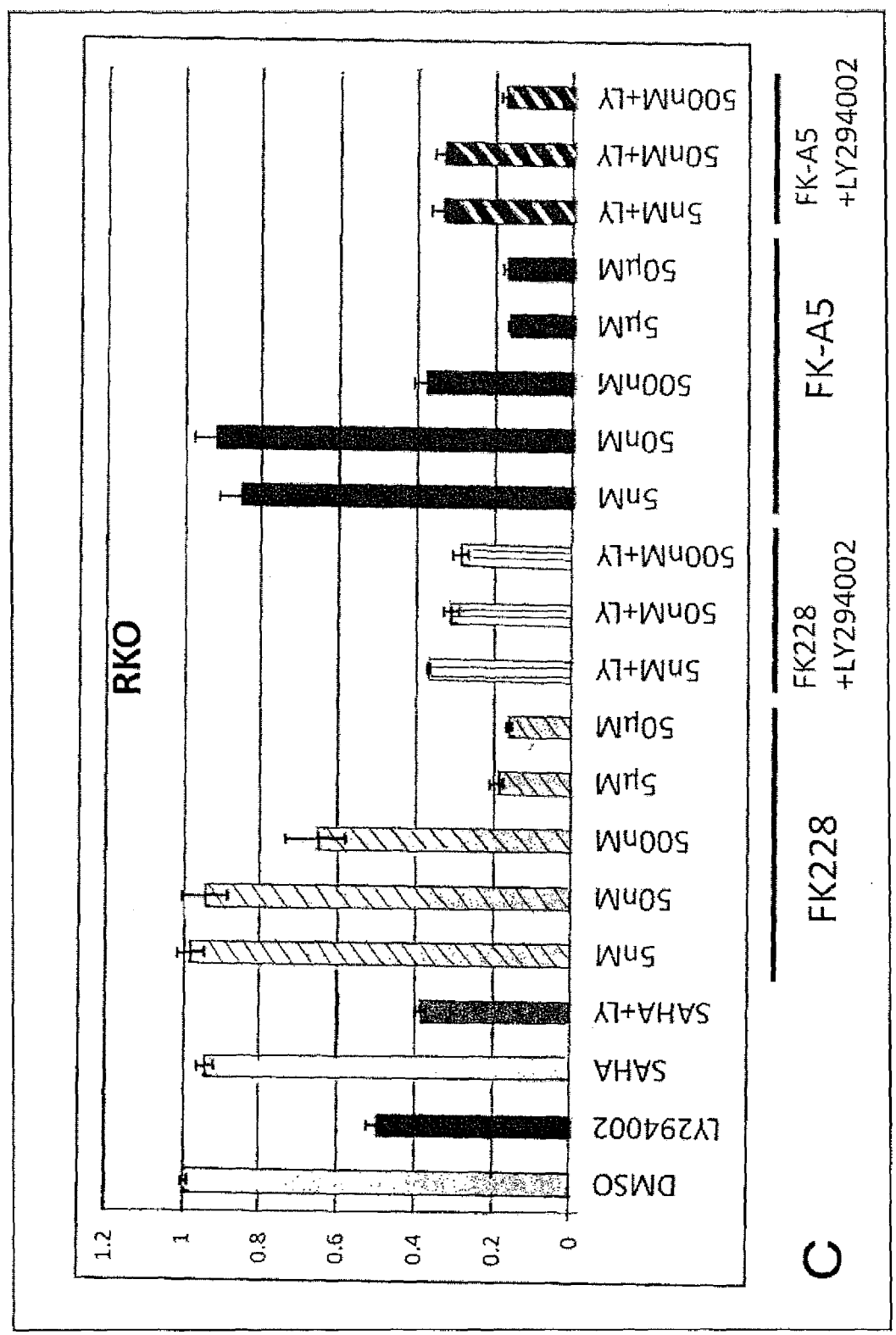

[Fig. 4D]
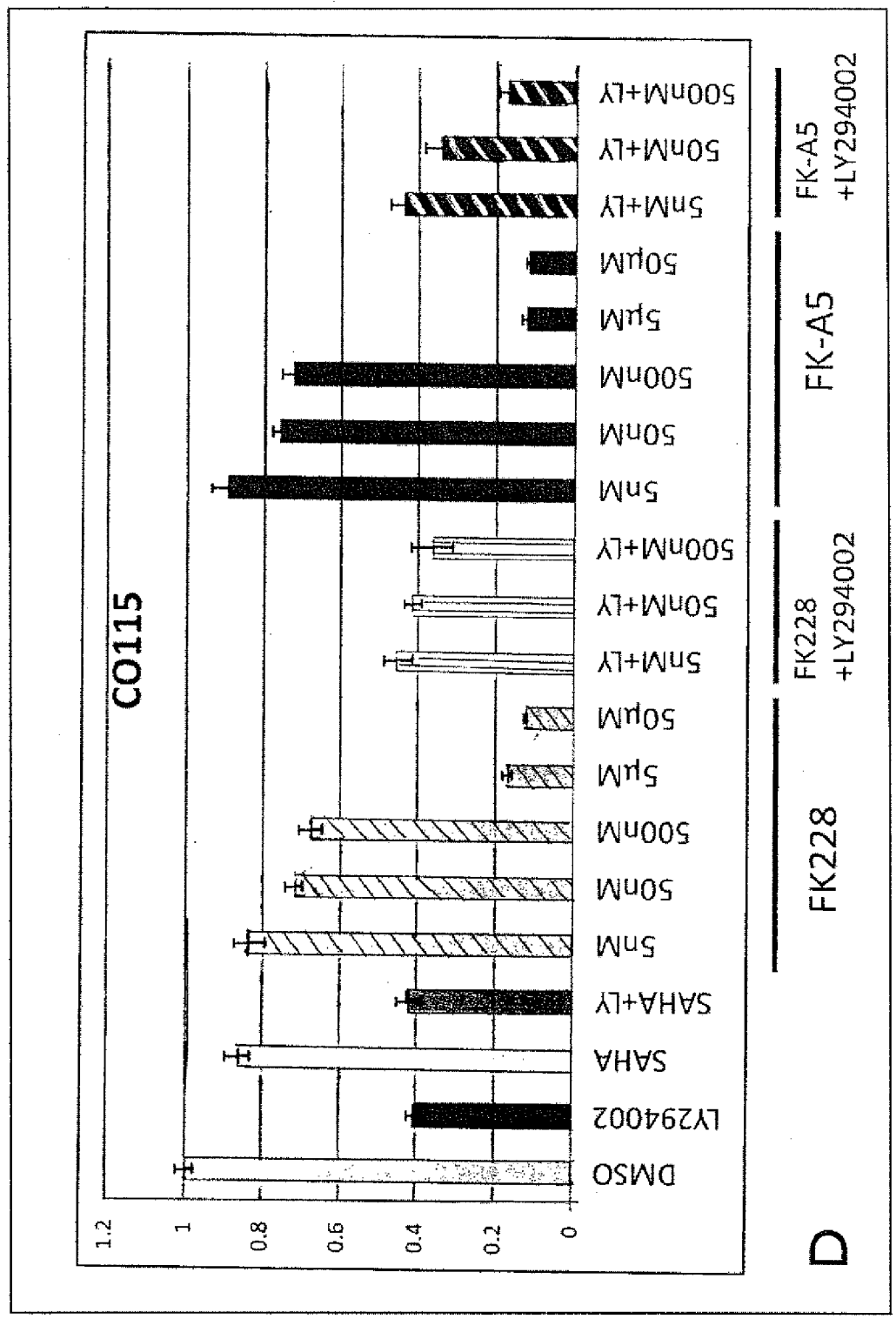

[Fig. 5A]
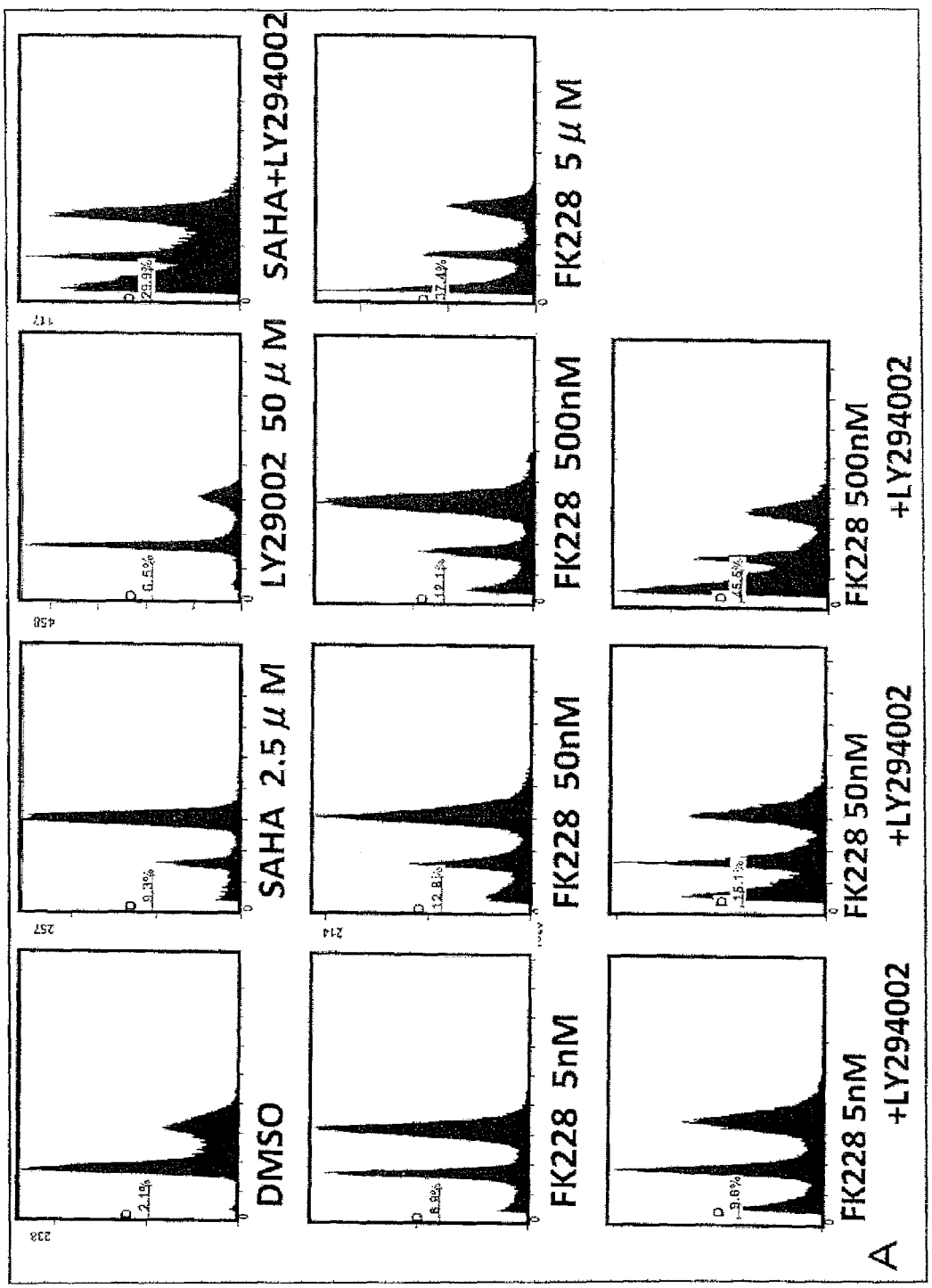

[Fig. 5B]
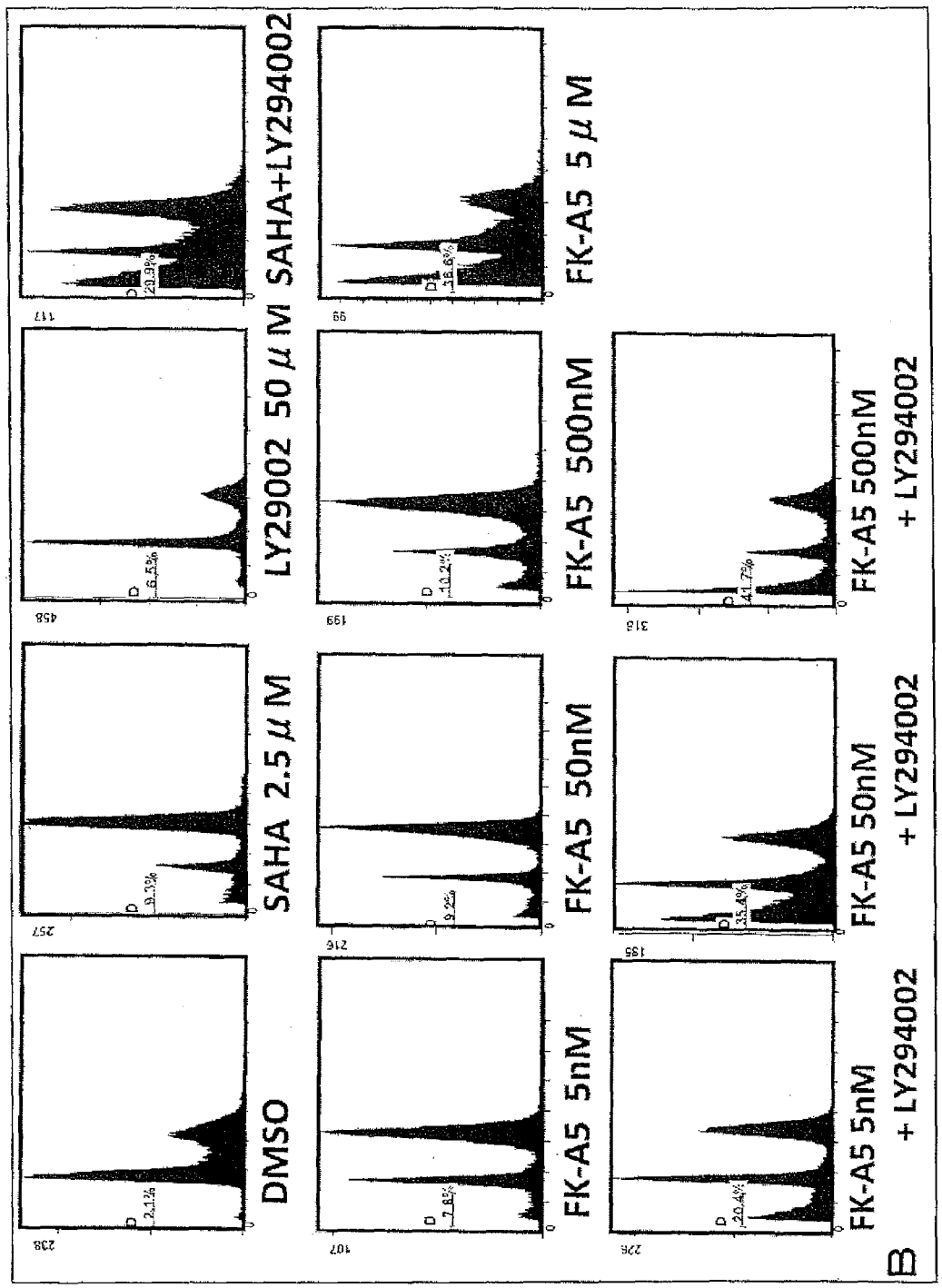

[Fig. 5C]
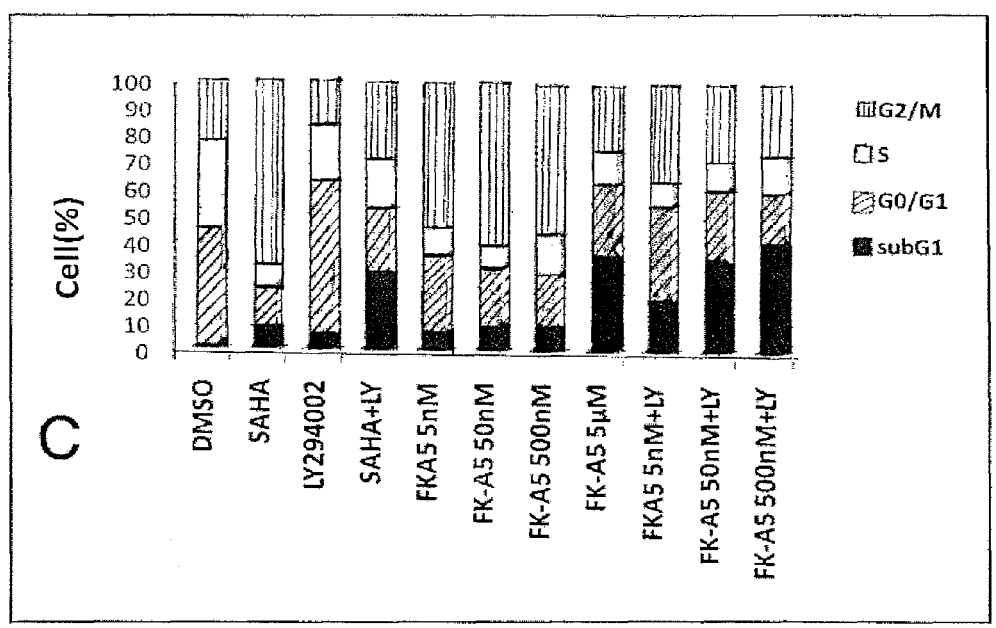

[Fig. 5D]
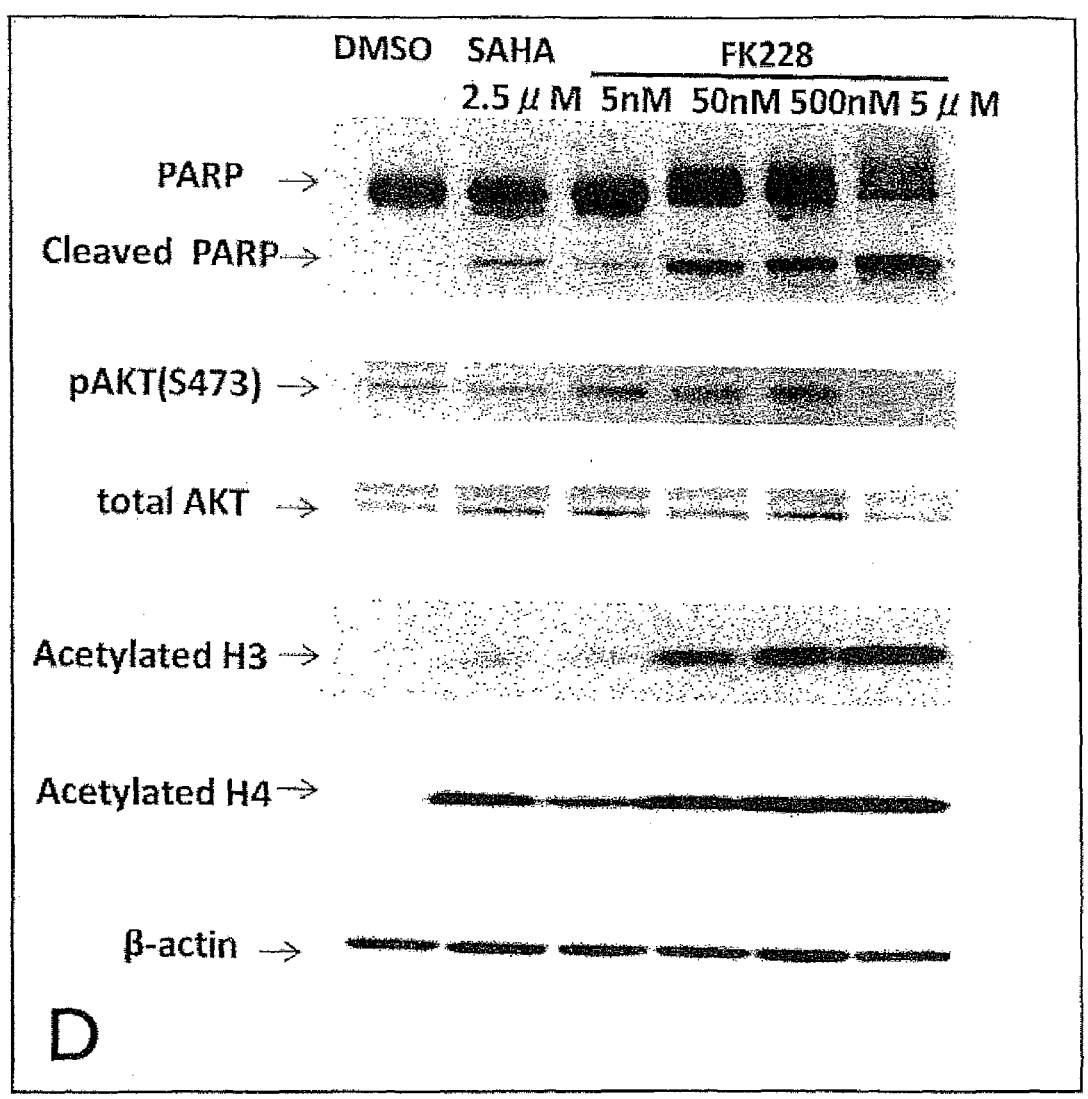

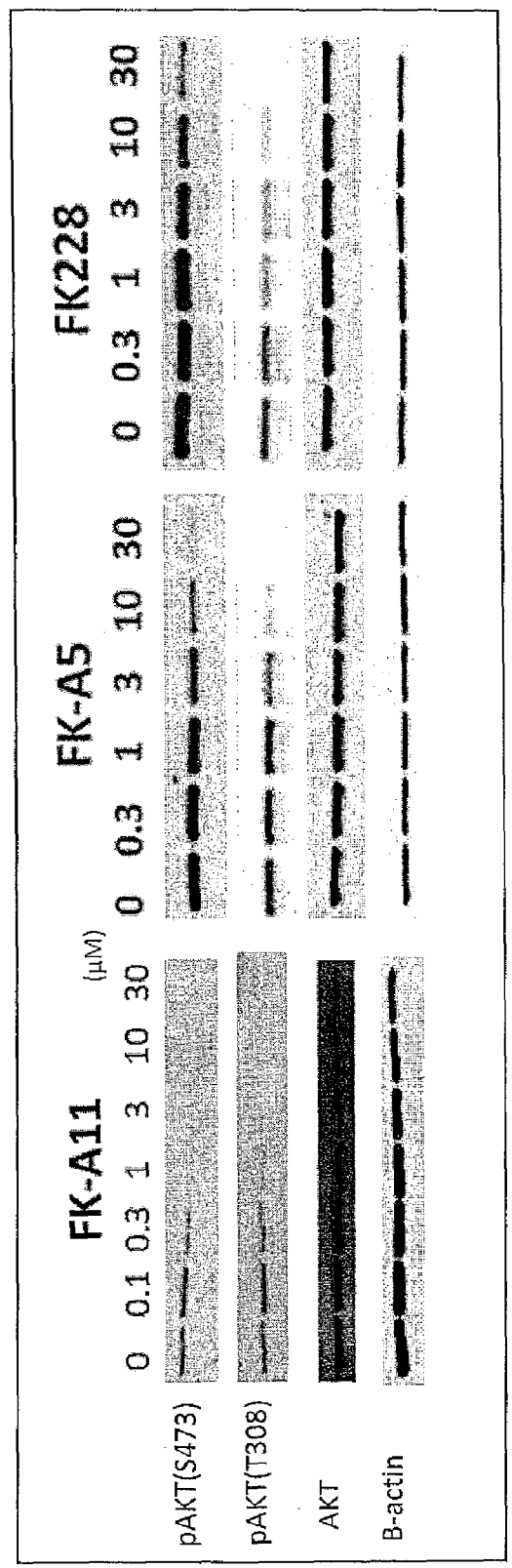
[Fig. 6]

[Fig. 7A]
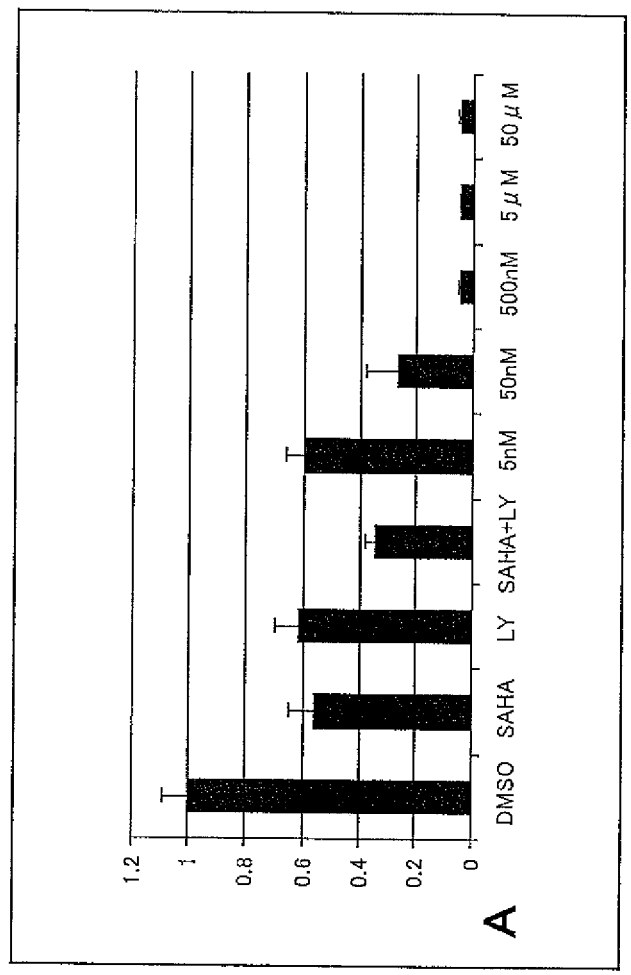

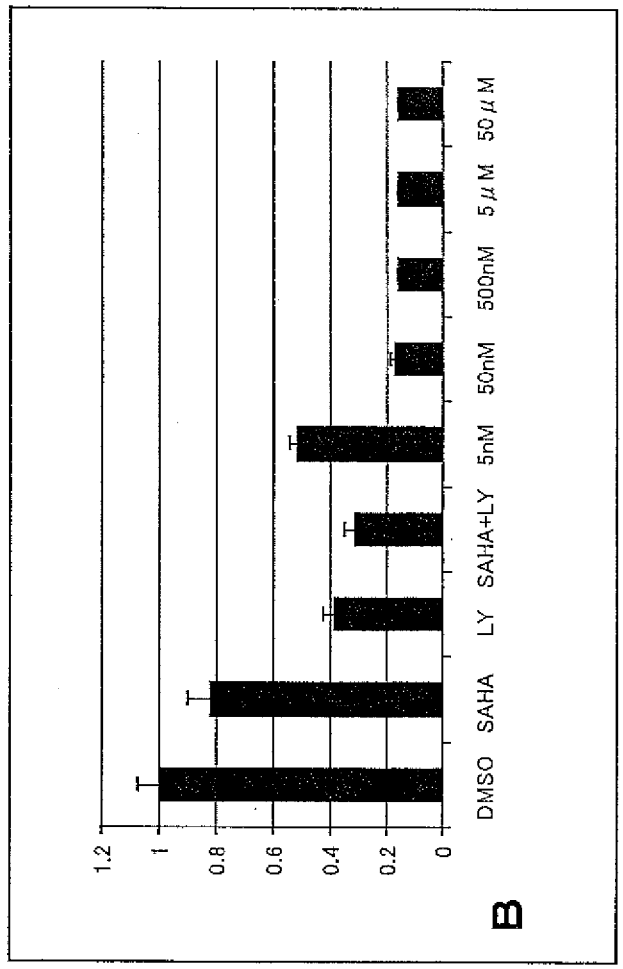
[Fig. 7B]

[Fig. 7C]
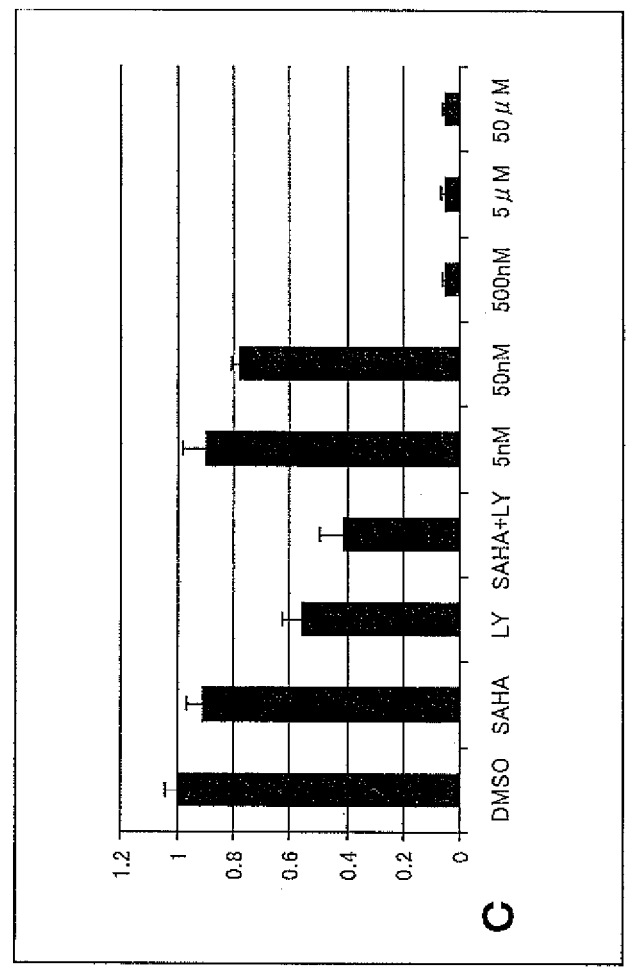

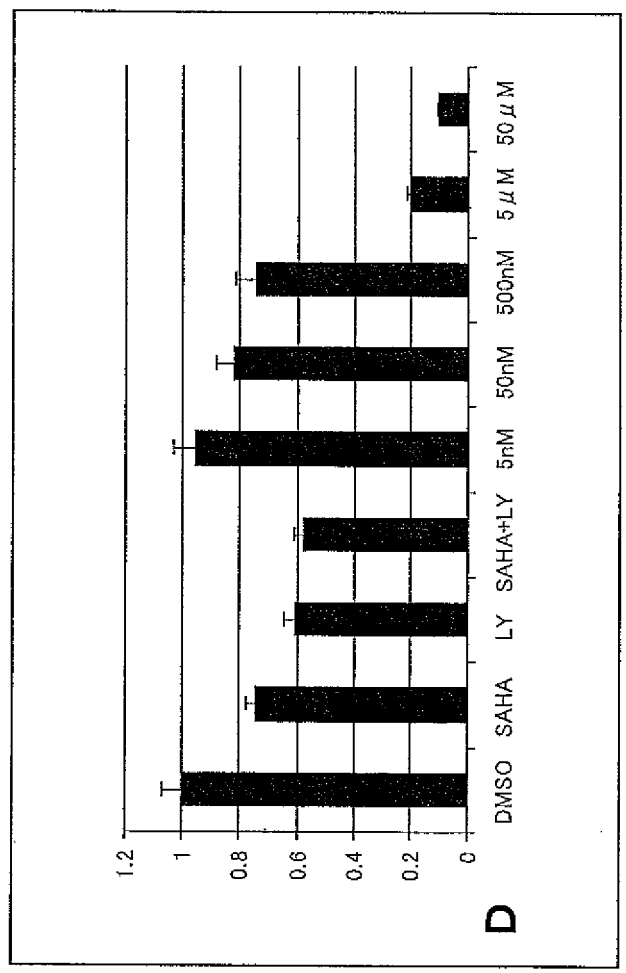
[Fig. 7D]

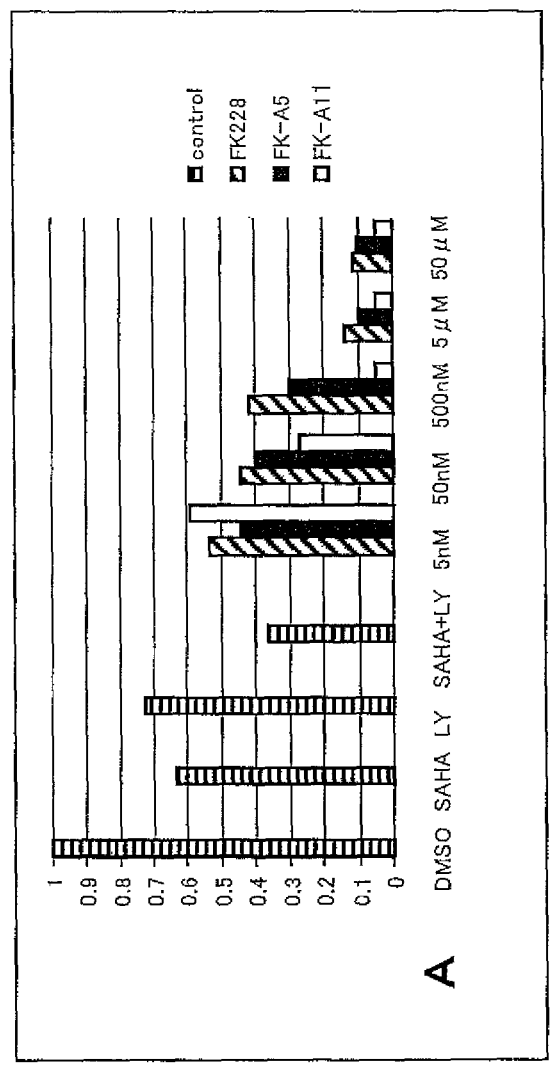
[Fig. 8A]

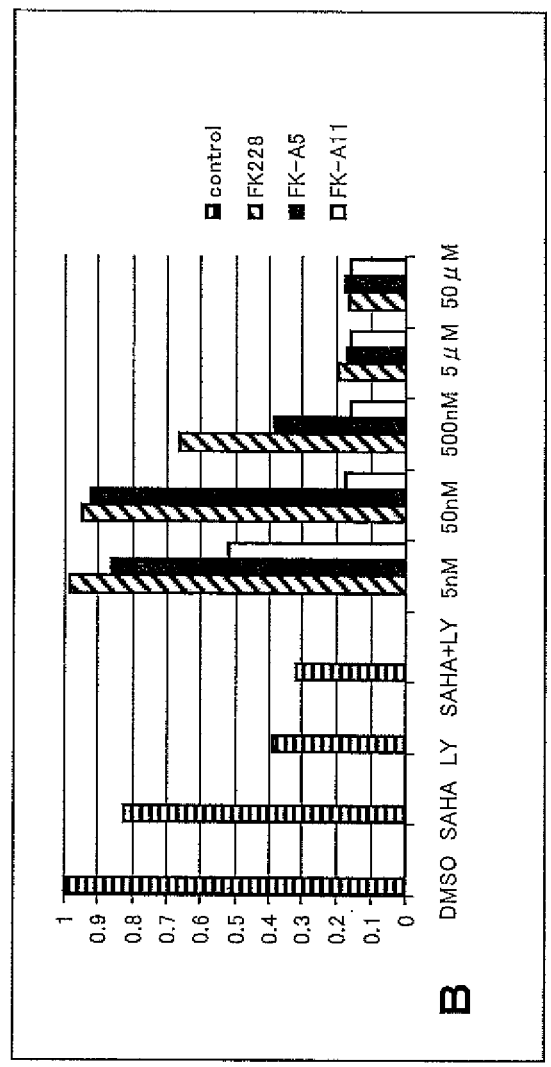
[Fig. 8B]

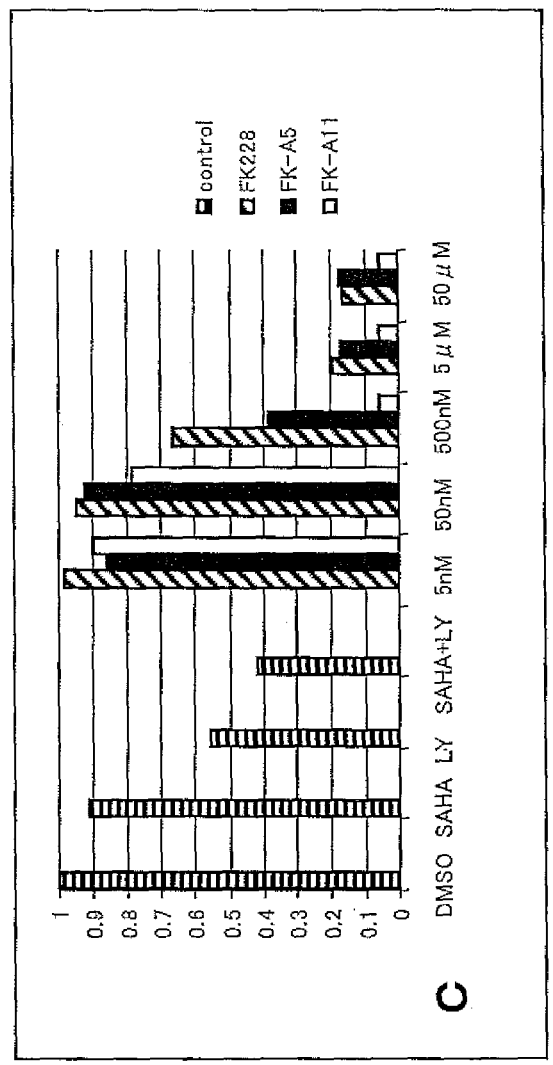
[Fig. 8C]

PHOSPHATIDYLINOSITOL-3-KINASE INHIBITOR AND PHARMACEUTICAL COMPOSITION

CROSS REFERENCE TO RELATED APPLICATIONS

This is a national stage application based on PCT/JP2012/074542, filed on Sep. 25, 2012, which claims priority to Japanese Patent Application No. 2011-217378, filed on Sep. 30, 2011. This application claims the priority of these prior applications and incorporates their disclosures by reference in their entireties.

TECHNICAL FIELD

The present invention relates to a novel phosphatidylinositol-3-kinase inhibitor and a pharmaceutical composition containing the same.

BACKGROUND ART

Chemotherapy against cancer has made a remarkable progress thanks to introduction of molecular targeted pharmaceuticals. However, there are still numerous refractory cancers that cannot be overcome. For such reasons, it is desired to develop new molecular targeted agents against cancer having a higher therapeutic effect.

Phosphatidylinositol-3-kinase (hereinbelow, referred to as "PI3K") is an enzyme which produces phosphatidyl inositol 3,4,5-triphosphate (PIP3) by phosphorylation of the phosphate group at position 3 of the inositol ring in phosphatidyl inositol 4,5-biphosphate (PIP2), which is a phospholipid present in a cell membrane (Non-Patent Document 1: Fruman et al., Annual Rev Biochem 67, 481-507, doi:10.1146/annurev. biochem. 67.1.481 (1998)). It is activated by tyrosine kinase of various growth factor receptors and, through the activation of AKT in downstream, it functions to promote survival and proliferation of cells (Non-Patent Document 2: Cantley, L. C. Science 296, 1655-1657, doi: 10.1126/science. 296.5573.1655 (2002)). PI3K is known to be involved with cancer.

PI3K forms a heterodimer consisting of a catalytic subunit and a regulatory subunit. PIK3CA gene encodes p110α, which is a catalytic subunit of Class IA PI3K. Regarding the PIK3CA gene, highly frequent gene amplification or point mutation of function developing type has been reported for various cancer types including breast cancer and colon cancer (Non-Patent Document 3: Samuels et al., Science 304, 554 (2004); Non-Patent Document 4: Ikenoue et al., Cancer Res 65, 4562 (2005); and Non-Patent Document 5: Kang et al., Proc. Natl. Acad. Sci. USA 102, 802 (2005)).

Further, the dephosphorylating enzyme PTEN (Phosphatase and tensin homologue deleted on chromosome 10), which catalyzes the reverse reaction of PI3K, inhibits cell proliferation by lowering PIP3 acting as a signal messenger (Non-Patent Document 6: Maehama et al., J. Biol. Chem. 273, 13375-13378 (1998)). With regard to PTEN gene, a deletion or a point mutation is found in many cancers like endometrial cancer and malignant melanoma (Non-Patent Document 7: Salmena et al., Cell 133, 403-414 (2008)), and it has been reported that the dephosphorylating enzyme activity is lowered in most cases of those point mutations (Non-Patent Document 8: Han et al., Cancer Res 60, 3147 (2000)).

In this regard, it is believed that abnormal continuous activation of the PI3K/AKT pathway is caused as a result of these mutations and the signal for cancer cell survival is transmitted.

Thus, PI3K receives attention as an important target molecule for cancer therapy, and development of a PI3K inhibitor is actively performed in recent years. Although several small molecule PI3K inhibitors are at a stage of clinical testing, so far none of them are established as a pharmaceutical product (Non-Patent Document 9: Kong & Yamori, Current Medicinal Chemistry 16, 2839-2854 (2009)).

Meanwhile, it has been known that an abnormality in epigenetics is deeply associated with an occurrence of cancer. Histone acetylation is one of the important mechanisms related to control of epigenetics (Non-Patent Document 10: Carew et al., Giles, Cancer Let 269, 7-17 (2008)), and it is found that, by the inhibition of a histone deacetylase (hereinbelow, referred to as "HDAC") which resolves the acetylation, a change in gene expression occurs, and cell differentiation or apoptosis occurs accompanying it. For such reasons, the HDAC inhibitor receives attention as a new molecular targeted agents against cancer.

A depsipeptide compound (Patent Documents 1 to 4) is a generic term for a peptide in which at least one amide bond (—CONHR—) is substituted with an ester bond (—COOR). Among the depsipeptide compounds, FK228 (FR901228, also referred to as romidepsin) is a compound isolated as a fermentation product from *Chromobacterium violaceum* (Non-Patent Document 11: Ueda et al., J. Antibiotics 47, 301 (1994)), and it is a potent HDAC inhibitor which selectively inhibits Class I HDAC (Non-Patent Document 12: Furumai et al., Cancer Res 62, 4916 (2002)). Based on the HDAC inhibiting activity, FK228 as an anti-cancer agent was subjected to a clinical testing, and together with suberoyl anilide hydroxamic acid (SAHA), which is also an HDAC inhibitor, was approved by U.S. FDA as a therapeutic agent for cutaneous T-cell lymphoma.

Meanwhile, although the term "depsipeptide" indicates FK228 in narrow sense, as used herein, it is used as a term having the meaning as described above.

It has been reported that the combined use of a PI3K inhibitor and an HDAC inhibitor results in an increase or synergistic effect in cytotoxic effect in human cancer cell lines (Non-Patent Document 13: Wozniak et al., Haematologica 95, 613 (2010)).

There has been a discussion as to whether or not the HDAC inhibitor itself has an influence on the PI3K/AKT pathway (Non-Patent Document 14: Hanker et al., J Molecular Signaling 4, 5 (2009); Non-Patent Document 15: Graham et al., Clinical Cancer Res 12, 223 (2006)). Trichostatin A (TSA), which is a classic HDAC inhibitor, has been reported to inhibit phosphorylated AKT via protein phosphatase 1 (Non-Patent Document 16: Chen et al., J Biol Chem 280, 38879 (2005)).

With regard to FK228, there is also a report indicating that it inhibits expression of phosphorylated AKT in a cell specific manner (Non-Patent Document 17: Kodani et al., Oncology Reports 13, 477-483 (2005)). However, the mechanism has not been clarified and also there is no document for determining the kinase inhibitory activity of FK228. It is also not reported that depsipeptide compounds have a PI3K inhibitory activity.

CITATION LIST

Patent Document

Patent Document 1: Official gazette of Japanese Provisional Patent Publication JP 2-85296 A
Patent Document 2: Official gazette of Japanese Provisional Patent Publication JP 4-79892 A
Patent Document 3: Official gazette of Japanese Provisional Patent Publication JP 2008-542347 W
Patent Document 4: Official gazette of Japanese Provisional Patent Publication JP 2009-519224 W Non-Patent Document Non-Patent Document 1: Fruman, D. A., Meyers, R. E. & Cantley, L. C. Annual Review of Biochemistry 67, 481-507, doi:10.1146/annurev.biochem.67.1.481 (1998)
Non-Patent Document 2: Cantley, L. C. Science 296, 1655-1657, doi:10.1126/science.296.5573.1655 (2002)
Non-Patent Document 3: Samuels, Y. et al. Science 304, 554 (2004)
Non-Patent Document 4: Ikenoue, T. et al. Cancer Research 65, 4562 (2005)
Non-Patent Document 5: Kang, S., Bader, A. G & Vogt, P. K. Proc. Natl. Acad. Sci. USA 102, 802 (2005)
Non-Patent Document 6: Maehama, T. & Dixon, J. E. The Journal of Biological Chemistry 273, 13375-13378 (1998)
Non-Patent Document 7: Salmena, L., Carracedo, A. & Pandolfi, P. P. Cell 133, 403-414 (2008)
Non-Patent Document 8: Han, S. Y. et at Cancer Research 60, 3147 (2000)
Non-Patent Document 9: Kong, D. & Yamori, T. Current Medicinal Chemistry 16, 2839-2854 (2009)
Non-Patent Document 10: Carew, J. S., Giles, F. J. & Nawrocki, S. T. Cancer Letters 269, 7-17 (2008)
Non-Patent Document 11: Ueda, H. et al. The Journal of Antibiotics 47, 301 (1994)
Non-Patent Document 12: Furumai, R. et al. Cancer Research 62, 4916 (2002)
Non-Patent Document 13: Wozniak, M. B. et al. Haematologica 95, 613 (2010)
Non-Patent Document 14: Hanker, A. B., Healy, K. D., Nichols, J. & Der, C. J. Journal of Molecular Signaling 4, 5 (2009)
Non-Patent Document 15: Graham, C. et al. Clinical Cancer Research 12, 223 (2006).
Non-Patent Document 16: Chen, C. S., Weng, S. C., Tseng, P. H. & Lin, H. P. Journal of Biological Chemistry 280, 38879 (2005)
Non-Patent Document 17: Kodani, M. et al. Oncology reports 13, 477-483 (2005)
Non-Patent Document 18: Tugendreich, S. et al. Genome Research 11, 1899 (2001)
Non-Patent Document 19: Rodriguez-Escudero, I. et al. Biochemical Journal 390, 613 (2005)
Non-Patent Document 20: Cid, V. et al. Oncogene 27, 5431-5442 (2008)
Non-Patent Document 21: "Search for novel PI3K inhibitor by using budding yeast as screening tool", Series No. P10-5, Abstract of the 15$^{th}$ Meeting of the Japanese Association for Molecular Target Therapy of Cancer, published on May 31, 2011
Non-Patent Document 22: Narita, K. et al. Chemistry—A European Journal 15, 11174-11186 (2009)
Non-Patent Document 23: Takizawa et al. Chemical Communication, 1677-1679 (2008)
Non-Patent Document 24: Takizawa et al. Heterocycles 76, 275-290 (2008)
Non-Patent Document 25: Rogers, B. et al. Journal of Molecular Microbiology and Biotechnology 3, 207-214 (2001)
Non-Patent Document 26: Alani, E., Cao, L. & Kleckner, N. Genetics 116, 541 (1987)
Non-Patent Document 27: Walker, E. H. et al. Molecular Cell 6, 909-919 (2000)
Non-Patent Document 28: Grunwald, V. et al. Cancer Research 62, 6141 (2002)
Non-Patent Document 29: Ropero, S. et al. Nature 200, 6
Non-Patent Document 30: Harrigan, C. L. et al. Gastroenterology 135, 1654-1664. e1652 (2008)
Non-Patent Document 31: Ree, A. H., Folkvord, S. & Flatmark, K. Nature Genetics 40, 812-813 (2008)
Non-Patent Document 32: Xu, W., Parmigiani, R. & Marks, P. Oncogene 26, 5541-5552 (2007)
Non-Patent Document 33: Richon, V. M., Sandhoff, T. W., Rifkind, R. A. & Marks, P. A. Proc. Natl. Acad. Sci. 97, 10014 (2000)
Non-Patent Document 34: Nakajima, H., Kim, Y. B., Terano, H., Yoshida, M. & Horinouchi, S. Experimental Cell Research 241, 126-133 (1998)
Non-Patent Document 35: Kumagai, T. et al. International Journal of Cancer 121, 656-665 (2007)

DISCLOSURE OF THE INVENTION

Problem to be Solved by the Invention

An object of the present invention is to provide a novel PI3K inhibitor. It is believed that development of pharmaceuticals inhibiting both PI3K and HDAC can significantly contribute to overcoming refractory cancer. Thus, another object of the present invention is to provide a substance that combines a PI3K inhibitory effect and an HDAC inhibitory effect. Finally, the present invention is also aimed to provide a novel anti-cancer pharmaceutical composition containing the substance, in particular an anti-cancer pharmaceutical composition that is effective even against refractory cancer.

Means for Solving Problem

In order to solve the problems described above, inventors of the present invention performed screening for identifying a novel PI3K inhibitor. Specifically, by using a screening system (Non-Patent Document 19; Non-Patent Document 21: "Search for novel PI3K inhibitor by using budding yeast as screening tool", Series No. P10-5, Abstract of the 15$^{th}$ Meeting of the Japanese Association for Molecular Target Therapy of Cancer, published on May 31, 2011) based on the phenomena that inhibition of cell proliferation is caused when human p110α is expressed in budding yeast but the inhibition of cell proliferation can be avoided by applying a PI3K inhibitor (Non-Patent Document 18: Tugendreich et al., Genome Research 11, 1899 (2001); Non-Patent Document 19: Rodriguez-Escudero et al., Biochemical Journal 390, 613 (2005); Non-Patent Document 20: Cid et al., Oncogene 27, 5431-5442 (2008)), compound library screening was performed. As a result, depsipeptide compounds that are HDAC inhibitors, namely, FK228 and its analogs, were selected as candidate compounds.

Inventors of the present invention demonstrated that, after performing in vitro evaluation of PI3K inhibitory activity, those compounds have a direct PI3K inhibitory activity at concentrations of μM order. Further, based on Western blot analysis using human culture cells, it was found that those compounds inhibited phosphorylated AKT and downstream molecules in the PI3K/AKT pathway. Further, based on the results of MTT assay, it was found that those compounds exhibited, within a specific concentration range, a potent cytotoxic effect even against the cells having resistance to an HDAC inhibitor. Still further, it was confirmed that the cell death was apoptosis and the apoptosis is induced by the double inhibitory activity of a depsipeptide compound on HDAC/PI3K, and the present invention was completed accordingly.

Accordingly, provided by the present invention is as follows:

[1] A phosphatidylinositol-3-kinase (PI3K) inhibitor comprising a depsipeptide compound represented by the formula 1 shown below:

[Chemical Formula 1]

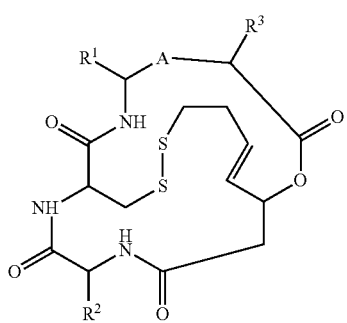

Formula 1

(wherein A represents —CONH— or —CH(OH)—, and $R^1$, $R^2$, and $R^3$ may be the same or different from each other and each represents a hydrogen atom, a lower alkyl group, a lower alkylidene group, a substituted or unsubstituted aryl group, or a substituted or unsubstituted aralkyl group), or a physiologically acceptable salt thereof;

[2] The PI3K inhibitor as described in the above [1], in which $R^3$ in the formula 1 is a hydrogen atom;

[3] The PI3K inhibitor as described in the above [1] or [2], in which $R^1$ in the formula 1 is a substituted or unsubstituted aralkyl group;

[4] A pharmaceutical composition for treatment of refractory cancer, characterized by containing, as an effective component, the PI3K inhibitor as described in any one of the above [1] to [3];

[5] The pharmaceutical composition for treatment of refractory cancer as described in the above [4], in which the PI3K inhibitor is administered at a dose of about 1 mg/day to 10,000 mg/day per kg of body weight;

[6] The pharmaceutical composition for treatment of refractory cancer as described in the above [4] or [5], in which the PI3K inhibitor is a depsipeptide compound represented by any one of the following formulae 2 to 20, or a physiologically acceptable salt thereof;

[Chemical Formula 2]

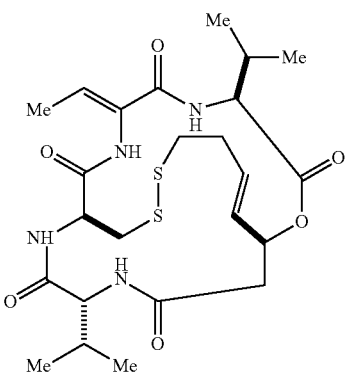

Formula 2

[Chemical Formula 3]

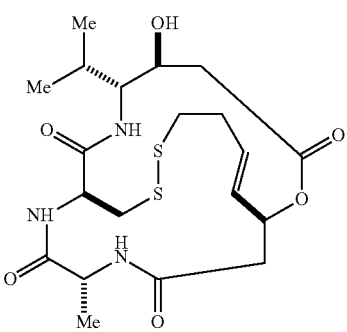

Formula 3

[Chemical Formula 4]

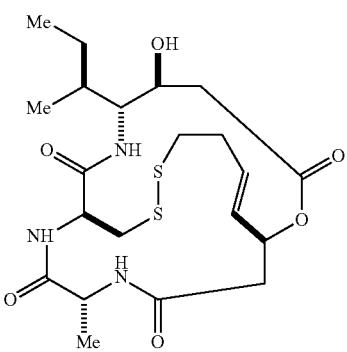

Formula 4

[Chemical Formula 5]

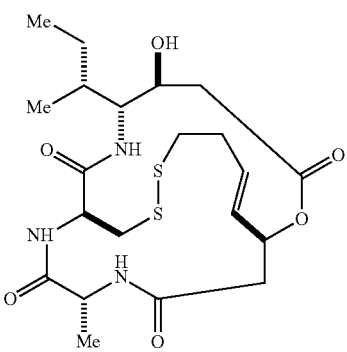

Formula 5

[Chemical Formula 6]
Formula 6
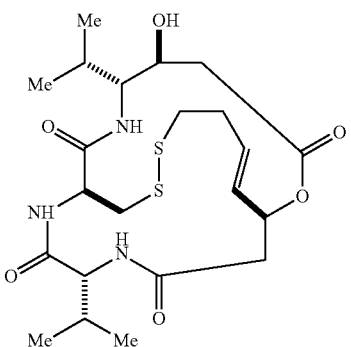
[Chemical Formula 7]
Formula 7
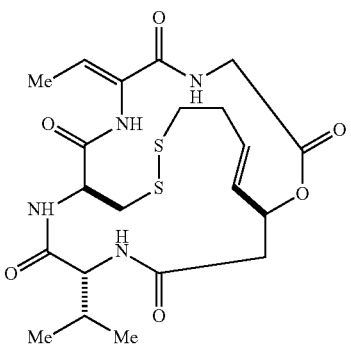
[Chemical Formula 8]
Formula 8
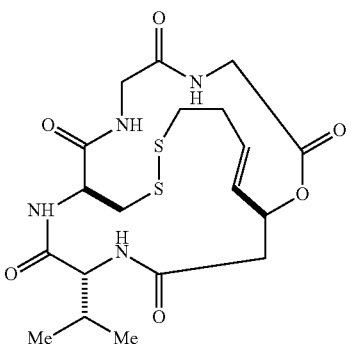
[Chemical Formula 9]
Formula 9
[Chemical Formula 10]
Formula 10
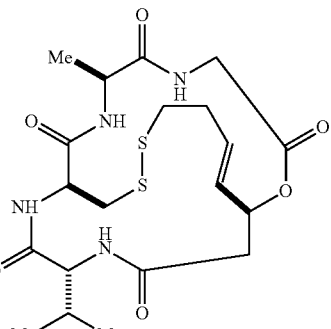
[Chemical Formula 11]
Formula 11
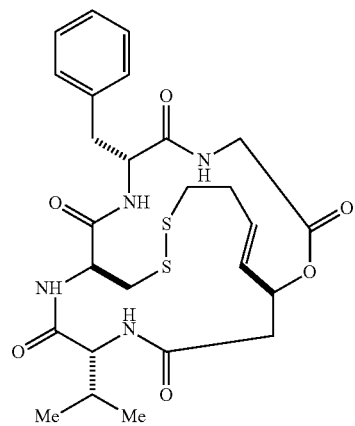
[Chemical Formula 12]
Formula 12
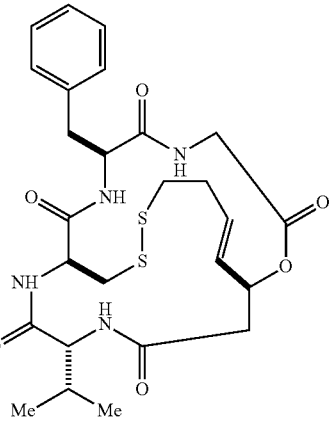
[Chemical Formula 13]
Formula 13
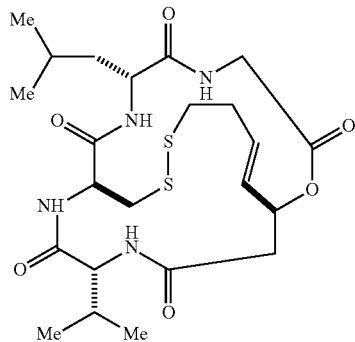

[Chemical Formula 14]
Formula 14
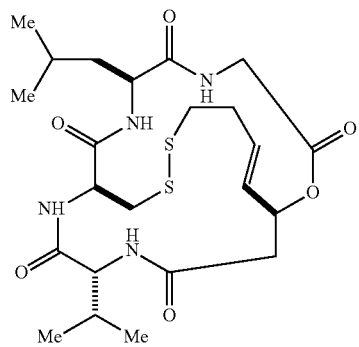
[Chemical Formula 15]
Formula 15
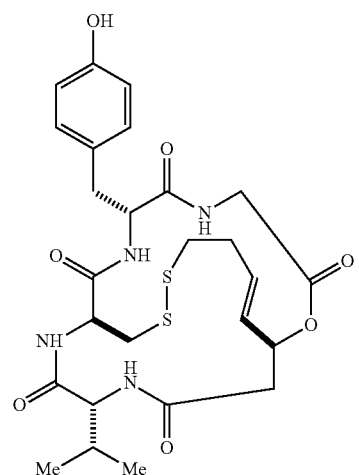
[Chemical Formula 16]
Formula 16
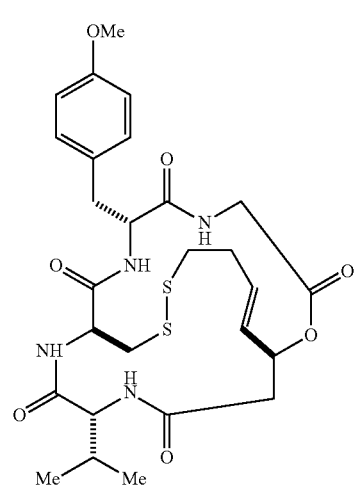
[Chemical Formula 17]
Formula 17
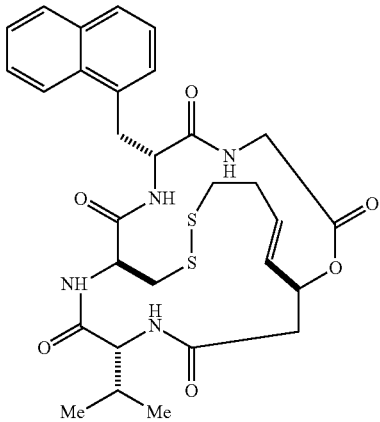
[Chemical Formula 18]
Formula 18
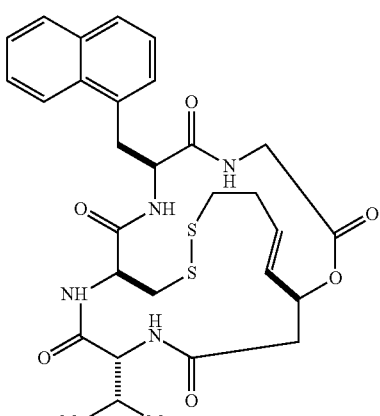
[Chemical Formula 19]
Formula 19
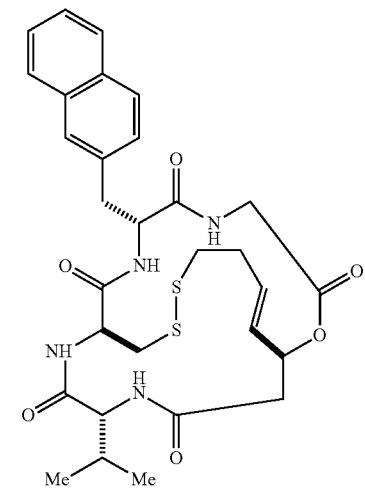

-continued

[Chemical Formula 20]

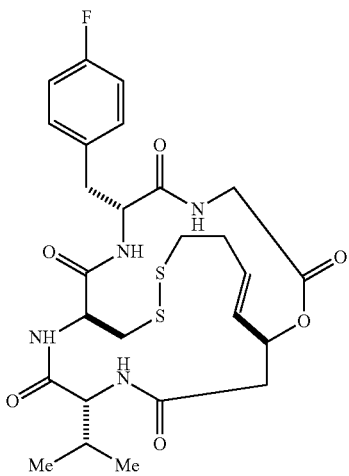

Formula 20

[7] A depsipeptide compound represented by the following formula 1:

[Chemical Formula 21]

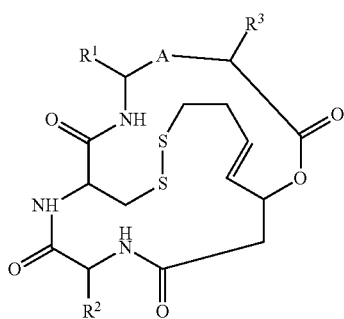

Formula 1

(wherein A represents —CONH— or —CH(OH)—, and $R^1$, $R^2$, and $R^3$ may be the same or different from each other and each represents a hydrogen atom, a lower alkyl group, a lower alkylidene group, a substituted or unsubstituted aryl group, or a substituted or unsubstituted aralkyl group; with the proviso that a compound having any of the following combinations of A, $R^1$, $R^2$, and $R^3$ is excluded: A=—CONH— and also $R^1$=an ethylidene group and also $R^2=R^3$=an isopropyl group, A=—CH(OH)— and also $R^1$=an isopropyl group and also $R^2$=a methyl group and also $R^3$=a hydrogen atom, A=—CH(OH)— and also $R^1$=a sec-butyl group and also $R^2$=a methyl group and also $R^3$=a hydrogen atom, A=—CH(OH)— and also $R^1=R^2$=an isopropyl group and also $R^3$=a hydrogen atom, A=—CONH— and also $R^1$=an ethylidene group and also $R^2$=an isopropyl group and also $R^3$=a hydrogen atom, A=—CONH— and also $R^1=R^3$=a hydrogen atom and also $R^2$=an isopropyl group, A=—CONH— and also $R^1$=a methyl group and also $R^2$=an isopropyl group and also $R^3$=a hydrogen atom, and A=—CONH— and also $R^1$=a benzyl group and also $R^2$=an isopropyl group and also $R^3$=a hydrogen atom), or a physiologically acceptable salt thereof.

Effect of the Invention

According to the present invention, a novel PI3K inhibitor is provided. The novel PI3K inhibitor is a compound with a structure that is completely different from that of a conventionally known PI3K inhibitor. The PI3K inhibitor of the present invention has an HDAC inhibitory activity and can also function as an HDAC inhibitor. However, when used at a specific concentration, it exhibits a cytotoxic activity by inducing apoptosis even against cancer cells having resistance to HDAC inhibitors. Thus, with the PI3K inhibitor of the present invention, a pharmaceutical composition effective for cancer cells which are resistant to a conventional anti-cancer agent containing an HDAC inhibitor can be provided.

Because the PI3K inhibitor of the present invention was found to have a possibility of inhibiting other kinases in addition to the HDAC inhibitory activity, there is a possibility that it is a multi-molecule targeting agent believed to be advantageous in controlling cancer cells.

Further, because the PI3K inhibitor of the present invention is used as a molecular targeted agent which specifically acts on cancer, it is believed that the influence exhibited on cells or tissues other than cancer cell is relatively minor. In fact, it is known for FK228 that it has no adverse effect even after administration for a long period of time and that, even when any adverse effect is caused, it is relatively minor, and it can be suppressed by combined use of a another agent for suppressing it. Analogs of FK228 are believed to cause a lower adverse effect than FK228 as described below, and thus the pharmaceutical composition of the present invention has a low possibility of causing a severe adverse effect even when it is used at a high dose in a living body.

BRIEF DESCRIPTION OF DRAWINGS

FIG. 1 is a drawing illustrating the pathway for synthesizing the compounds of the present invention, in which "Boc"=tert-butoxycarbonyl, "TBS"=tert-butyldimethylsilyl, "Tr"=trityl, and "PMB"=p-methoxybenzyl.

FIG. 2A is a drawing illustrating the measurement of the PI3K inhibitory activity of FK228 and analogs thereof. The PI3K inhibitory activity of FK228 and analogs thereof (SP-1, SP-2, SP-3, SP-5, FK228, FK-A1, FK-A2, FK-A3, FK-A4, FK-A5, and FK-A6) at 20 μM is shown as PI3K activity inhibitory rate.

FIG. 2B is the PI3K inhibitory curve of LY294002 according to the same measurement. The vertical axis represents the inhibitory rate against PI3K activity.

FIG. 2C is the PI3K inhibitory curve of FK228 according to the same measurement. The vertical axis represents the inhibitory rate against PI3K activity.

FIG. 2D is the PI3K inhibitory curve of FK-A5 according to the same measurement. The vertical axis represents the inhibitory rate against PI3K activity.

FIG. 2E is the PI3K inhibitory curve of FK228 according to the same measurement with different ATP concentration conditions. The vertical axis represents the inhibitory rate against PI3K activity. The solid line represents the results at ATP concentration of 50 μM and the broken line represents the results at ATP concentration of 500 μM.

FIG. 3 is a drawing illustrating the evaluation of inhibition of the AKT pathway as determined by Western blotting. Panel A represents changes in phosphorylated AKT in accordance with the compound treatment time. After applying LY294002, FK228, or FK-A5, each at 10 μM, to PC3 cells for 5 minutes, 30 minutes, or 180 minutes, the cells were collected, and the results of phosphorylated (p-)AKT and AKT detected by Western blotting are shown. Panel B represents the inhibition of the AKT pathway in accordance with the change in concentrations of FK228 or FK-A5. It is a drawing illustrating the results obtained by treating PC3 cells with FK228 or FK-A5 at concentrations (µM) shown in the drawing for 180 minutes, collecting the samples and subjecting them to Western blot analysis for determination of the expression levels of phosphorylated AKT (Ser-473, Thr-308), and AKT, phosphorylated GSK-3β (Ser-9), phosphorylated mTOR (Ser-2448), phosphorylated p70S6K (Thr-389), phosphorylated 4E-BP1 (Thr-37/46), phosphorylated MEK1/2 (Ser-217/221), and phosphorylated ERK1/2 (Thr-202/Tyr-204).

FIG. 4A is a drawing illustrating the results of the expression of HDAC2 and HDAC1 in HCT116 cells, RKO cells, and CO115 cells confirmed based on Western blotting.

FIG. 4B is a drawing illustrating the evaluation of cytotoxic effect of FK228 and FK-A5 in HCT116 cells. It represents results which is obtained by incubating the cells for 24 hours in the presence of LY294002 (50 µM), SAHA (2.5 µM), or the combined use of the same concentrations of LY294002 (50 µM) and SAHA (2.5 µM) (SAHA+LY), or FK228, FK-A5, or the combined use of the same concentrations of FK228 or FK-A5 and LY294002, performing MTT analysis, and counting the number of viable cells to determine the cytotoxic effect. The vertical axis of the graph represents the ratio against the absorbance when DMSO was added.

FIG. 4C is a drawing illustrating the evaluation of cytotoxic effect of FK228 or FK-A5 in RKO cells, which was measured in the same manner as FIG. 4B.

FIG. 4D is a drawing illustrating the evaluation of cytotoxic effect of FK228 or FK-A5 in CO115 cells, which was measured in the same manner as FIG. 4A.

FIG. 5A is a drawing illustrating the results of FACS analysis of HCT116 cells, which were cultured for 24 hours in the presence of FK228 at the concentrations shown in the drawing or FK228 and LY294002 (50 µM). The upper row shows the results for comparison which were obtained from the treatment with 50 µM LY294002, 2.5 µM SAHA, and the same concentrations of LY294002 (50 µM) and SAHA (2.5 µM).

FIG. 5B is a drawing illustrating the results of an analysis which were obtained in the same manner as FIG. 5A by using FK-A5 instead of FK228.

FIG. 5C is a drawing illustrating the results of calculating percentage of G2/M, S, G1/G0, and subG1 fractions based on the analysis of FIG. 5B for FK-A5.

FIG. 5D is a drawing illustrating the results of Western blot analysis for expression of PARP, cleaved PARP, phosphorylated AKT (S473), AKT, acetylated histone H3, and acetylated histone H4 following the treatment of the HCT116 cells with SAHA or FK-228 at the concentrations shown in the drawing for 24 hours.

FIG. 6 is a drawing illustrating the evaluation of inhibition of the AKT pathway based on Western blotting, which was performed in the same manner as the test shown in panel B of FIG. 3. From the left side, inhibition of the AKT pathway in accordance with a change in concentrations of FK-A11, FK-A5, or FK228 is shown. It is a drawing illustrating the results obtained by treating PC3 cells with each compound at concentrations (µM) shown in the drawing for 180 minutes, collecting the samples and subjecting them to Western blot analysis for determination of the expression level of phosphorylated AKT (Ser-473, Thr-308) and AKT.

FIG. 7A is a drawing illustrating the evaluation of cytotoxic effect of FK-A11 in HCT116 cells. It represents results which were obtained by incubating the cells for 24 hours in the presence of LY294002 ("LY"; 50 µM), SAHA (2.5 µM), or the combined use of the same concentrations of LY294002 (50 µM) and SAHA (2.5 µM) (SAHA+LY), and FK-A11 at the concentrations shown in the drawing, performing MTT analysis, and counting the number of viable cells to determine the cytotoxic effect. The vertical axis of the graph represents the ratio against the absorbance when DMSO was added.

FIG. 7B is a drawing illustrating the evaluation of cytotoxic effect of FK-A11 in RKO cells, which was measured in the same manner as FIG. 7A.

FIG. 7C is a drawing illustrating the evaluation of cytotoxic effect of FK-A11 in CO115 cells, which was measured in the same manner as FIG. 7A.

FIG. 7D is a drawing illustrating the evaluation of cytotoxic effect of FK-A11 in KMST6 cells as normal cells (non-cancerous, fibroblast cells), which was measured in the same manner as FIG. 7A.

FIG. 8A is a drawing illustrating the comparison of the cytotoxic effect of FK228, FK-5, and FK-A11 in HCT116 cells, which was measured in the same manner as FIG. 7A. Bars with horizontal lines represent the control (DMSO, SAHA, LY, or SAHA+LY), bars with oblique lines represent FK228, filled bars represent FK-5, and empty bars represent FK-A11.

FIG. 8B is a drawing illustrating the evaluation of cytotoxic effect of FK228, FK-5, and FK-A11 in RKO cells, which was measured in the same manner as FIG. 7A. Bars with horizontal lines represent the control (DMSO, SAHA, LY, or SAHA+LY), bars with oblique lines represent FK228, filled bars represent FK-5, and empty bars represent FK-A11.

FIG. 8C is a drawing illustrating the evaluation of cytotoxic effect of FK228, FK-5, and FK-A11 in CO115 cells, which was measured in the same manner as FIG. 7A. Bars with horizontal lines represent the control (DMSO, SAHA, LY, or SAHA+LY), bars with oblique lines represent FK228, filled bars represent FK-5, and empty bars represent FK-A11.

MODE(S) FOR CARRYING OUT THE INVENTION

The PI3K inhibitor of the present invention is characterized in that it comprises the depsipeptide compound represented by the following formula 1 or a physiologically acceptable salt thereof.

[Chemical Formula 22]

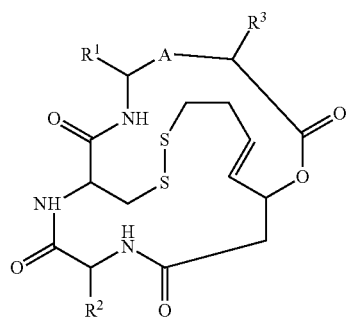

Formula 1

(In the formula, A represents —CONH— or —CH(OH)—, and $R^1$, $R^2$, and $R^3$ may be the same or different from each other and each represent a hydrogen atom, a lower alkyl group, a lower alkylidene group, a substituted or unsubstituted aryl group, or a substituted or unsubstituted aralkyl group).

It is preferable that $R^1$ be a hydrogen atom, a lower alkyl group, a lower alkylidene group, or a substituted or unsubstituted aralkyl group, $R^2$ be a lower alkyl group, and $R^3$ be a hydrogen atom or a lower alkyl group. In the present invention, examples of the "lower alkyl group" include a linear or branched alkyl group having 1 to 6 carbon atoms such as methyl, ethyl, n-propyl, i-propyl, cyclopropyl, n-butyl, s-butyl, t-butyl, cyclobutyl, n-pentyl, i-pentyl, 2-methylbutyl, cyclopentyl, n-hexyl, and cyclohexyl. Examples of the "lower alkylidene group" include a linear or branched alkylidene group having 1 to 6 carbon atoms such as methylene, ethylidene, propylidene, cyclopropylidene, butylidene, pentylidene, and hexylidene. Examples of the "aryl group" include phenyl, naphthyl, pyridinyl, and furanyl, and examples of the substituent group for them include a hydroxyl group, a hydroxyl group protected with a protecting group, an amino group, and an amino group protected with a protecting group. Examples of the "aralkyl group" include benzyl, 1-phenylethyl, naphthylmethyl, and pyridinylmethyl, and examples of the substituent group for them include a hydroxyl group, a hydroxyl group protected with a protecting group, an amino group, and an amino group protected with a protecting group.

Examples of the particularly preferred compounds include the following compounds.

[Chemical Formula 23]

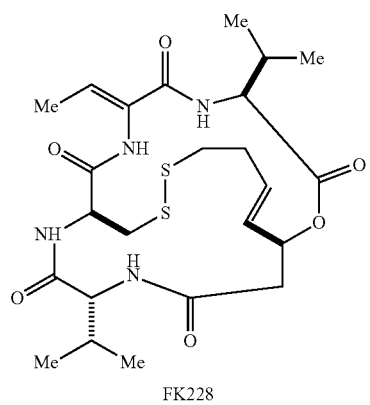

FK228

[Chemical Formula 24]

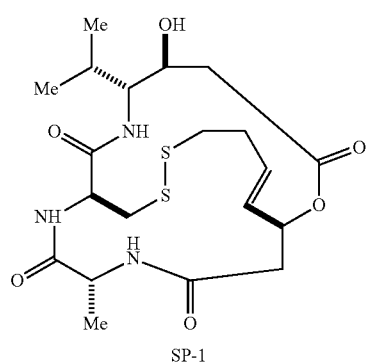

SP-1

[Chemical Formula 25]

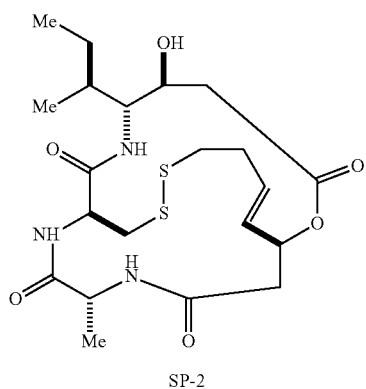

SP-2

[Chemical Formula 26]

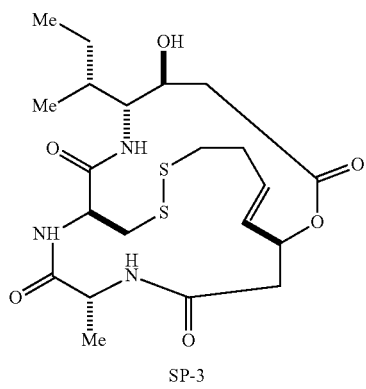

SP-3

[Chemical Formula 27]

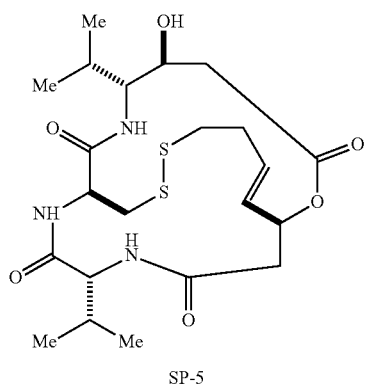

SP-5

[Chemical Formula 28]

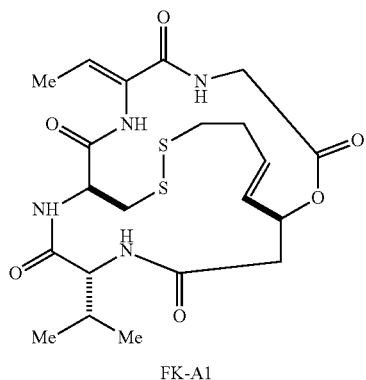

FK-A1

[Chemical Formula 29]
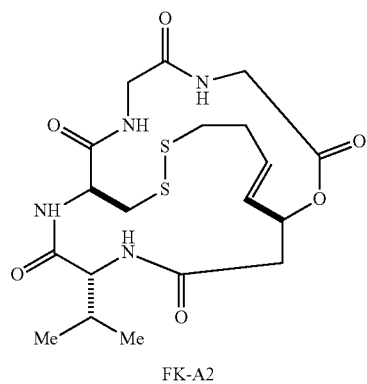
FK-A2
[Chemical Formula 30]
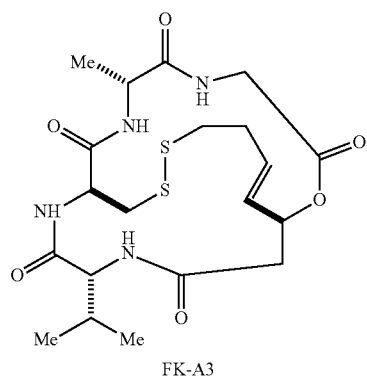
FK-A3
[Chemical Formula 31]
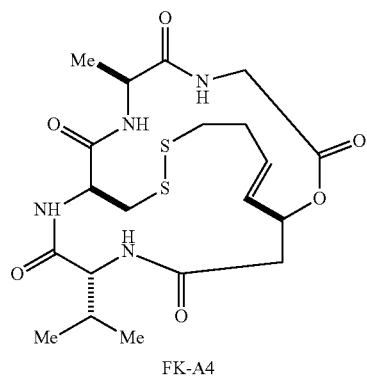
FK-A4
[Chemical Formula 32]
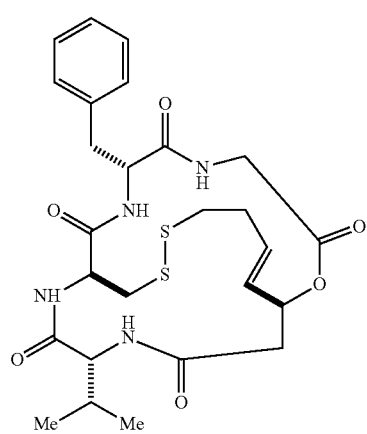
FK-A5
[Chemical Formula 33]
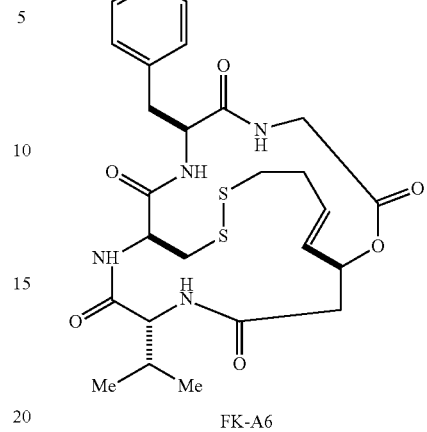
FK-A6
[Chemical Formula 34]
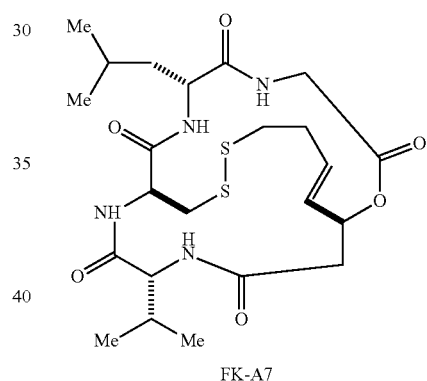
FK-A7
[Chemical Formula 35]
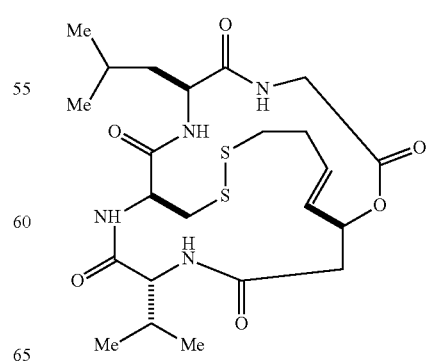
FK-A8

[Chemical Formula 36]

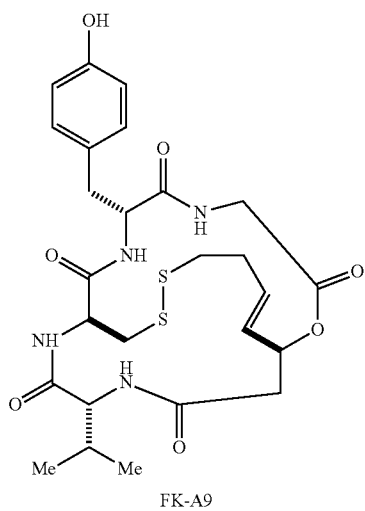

FK-A9

[Chemical Formula 37]

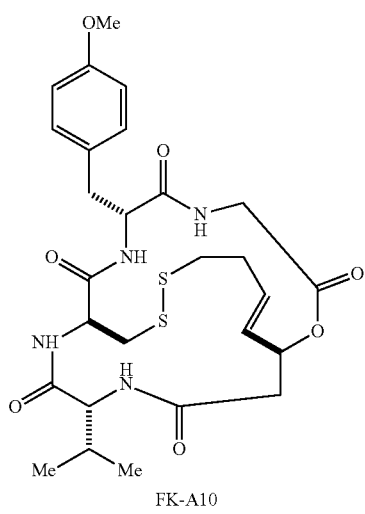

FK-A10

[Chemical Formula 38]

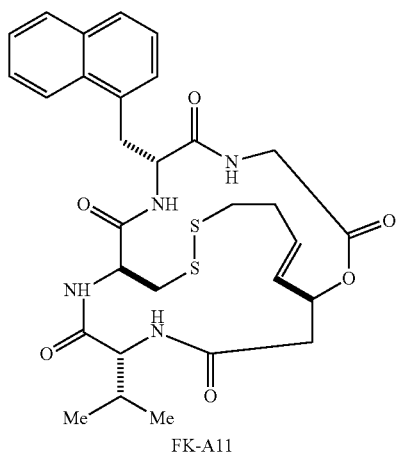

FK-A11

[Chemical Formula 39]

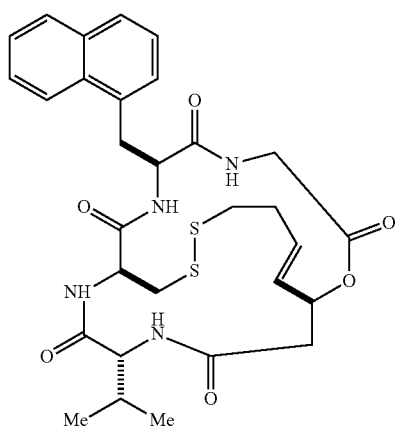

FK-A12

[Chemical Formula 40]

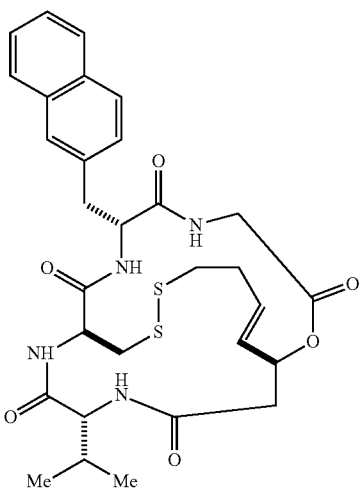

FK-A13

[Chemical Formula 41]

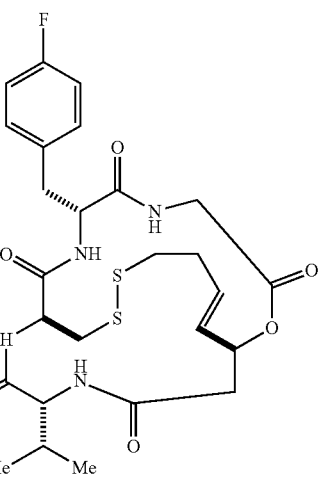

FK-A17

More preferred are those in which $R^3$ is a hydrogen atom and/or $R^1$ is a substituted or unsubstituted aralkyl group.

Further, as for the PI3K inhibitor of the present invention, specific examples of the physiologically acceptable salts include an inorganic salt (sodium salt, potassium salt, and lithium salt; calcium salt and magnesium salt; aluminum salt, iron salt, zinc salt, copper salt, nickel salt, and cobalt salt; and ammonium salt), and various organic salts, halogenated hydrogen acid salts, inorganic acids salts, organic acid salts, and amino acid salts.

In the present invention, one type or two or more types of the depsipeptide compounds or a salts thereof can be suitably selected and used.

The method for preparing the depsipeptide compounds of the present invention, namely, FK228 and the analogs, is known. FK228 can be obtained by isolating and purifying a natural product produced by microorganisms, or it can be also produced by semi-synthesis or total synthesis according to a method known in related art. Specifically, the synthesis of the compound of the present invention can be performed according to the methods described in Narita et al., Chemistry—A European Journal 15, 11174-11186 (2009) (Non-Patent Document 22); Takizawa et al., Chemical Communication, 1677-1679 (2008) (Non-Patent Document 23); and Takizawa et al., Heterocycles 76, 275-290 (2008) (Non-Patent Document 24).

Cancer to be treated with the pharmaceutical composition of the present invention includes various cancers for which effectiveness of FK228 is known, and particularly intractable types of cancer. Specific examples include skin cancer, mesothelioma, lung cancer, stomach cancer, liver cancer, colon cancer, breast cancer, esophageal cancer, pancreatic cancer, uterine cancer (cervical cancer and endometrial cancer), ovarian cancer, skin cancer, urological cancer, head and neck cancer, cancer of unknown primary site, hematologic malignancies (leukemia and lymphoma), and bone soft tissue sarcoma, and those showing no effect or little effect by other treatment. Further, the present agent is expected to be particularly effective for cancers for which highly frequent mutation in PIK3 CA gene has been reported, including breast cancer, uterine endometrial cancer, urological cancer, colon cancer, ovarian cancer, head and neck cancer, and lung cancer (Non-Patent Document 3).

The pharmaceutical composition of the present invention can be suitably prepared by a method known in the pertinent art using the PI3K inhibitor of the present invention and various additives or the like that are known in the pharmaceutical industry.

Routes of administration for the pharmaceutical composition of the present invention can be any route selected from known routes such as oral, nasal, under tongue, eye drop, transdermal, injection, enteral, and intrarectal. Preferably, it is an oral route or injection.

Thus, the pharmaceutical composition of the present invention can be provided as a formulation including, in addition to an orally administered formulation (a tablet, a granule, a capsule, powder, or the like) and a formulation for injection, a suppository, a patch, an infusion, a hydrous agent, an eye drop, and a troche. The method for producing those various formulations are fully known to a skilled person in the pertinent art.

Depending on a desired formulation type, various kinds of a vehicle, a disintegrating agent, a lubricating agent, a binder, a surfactant, a fluidity promoting agent, a coloring agent, a fragrance, or the like that are used as additives in the pharmaceutical industry can be suitably used for production of the pharmaceutical composition of the present invention.

The pharmaceutical composition of the present invention may also contain other known pharmaceutically effective components. Examples thereof include an anti-vomiting agent, a digestive, and an other anti-cancer agent.

The pharmaceutical composition of the present invention may be combined with a known drug delivery system. Examples thereof include liposome, inorganic nano particles, inorganic-organic hybrid nano particles, and an implant.

By further containing those other effective components or using the pharmaceutical composition of the present invention in combination with other pharmaceutical agents, more improved therapeutic effect is expected.

The dose and formulation for administration of the pharmaceutical composition of the present invention can be determined depending on the type of cancer to be treated, an administration method, as well as the age, weight, or disorder condition of a patient to receive the administration.

In terms of effective components, about 1 mg/day to 10,000 mg/day in general, more preferably about 10 mg/day to about 5,000 mg/day, even more preferably about 20 mg/day to about 5,000 mg/day, and most preferably about 50 mg/day to about 5,000 mg/day per kg of body weight can be administered once a day or two or three times per day in divided portions to a patient who is believed to be in need of the treatment with the pharmaceutical composition of the present invention.

EXAMPLES

1. Screening of PI3K Inhibitor Using Budding Yeast

The screening system used in the present invention is based on a cell proliferation disorder caused by the expression of human p110α in budding yeast, and the screening was performed basically according to the method described by Rodriguez-Escudero and others (Non-Patent Document 19: Biochemical Journal 390, 613 (2005)). For the present screening, however, a drug-sensitive strain, AD1-9, in which seven ABS transporter genes and the genes of two transcription factors related to activation of ABC transporter have been knocked out (MAT alpha, yor1, snq2, pdr5, pdr10, pdr11, ycf1, pdr3, pdr15, pdr1, his1, ura3) (Non-Patent Document 25: Rogers et al., J. of Mol. Microbiol. Biotechnol. 3, 207-214 (2001)) was used instead of the commonly used wild type strain YPH499. AD1-9 strain can be obtained from Nader Nourizad (Stanford Genome Technology Center Stanford University, CA, USA).

To add an auxotrophic marker to AD 1-9, the inventors of the present invention produced LEU2 gene-disrupted AD 1-9 strain according to the method using hisG-Ura3-hisG cassette (Non-Patent Document 26: Alani et al., Genetics 116, 541 (1987)) and used it.

The transformed AD 1-9 strain was cultured at 30° C. in a minimal complete medium SC-U-L containing no uracil and leucine or SGal-U-L in which 2% glucose was replaced with 2% galactose.

As a result of evaluating a difference in sensitivity of those yeast strains for LY294002 (purchased from Cayman Chemical Company), which is a known PI3K inhibitor, recovery from the cell proliferation disorder with LY294002 was observed in YPH499 at the concentration of 50 μM, while it was observed at 5 μM in AD1-9 which was used for the screening. Thus, it was confirmed that AD 1-9 used for the screening had the sensitivity for LY294002 which was about ten times higher than that of YPH499.

By using the aforementioned system, screening of the compound library, which was obtained from the Screening committee of anticancer drugs supported by grant-in-aid for scientific research on priority area "Cancer" from Ministry of Education, Culture, Sports, Science, and Technology, Japan, was performed. Each compound was added to SGal- U-L liquid medium to constitute a concentration of 0.5 µM or 5 µM and the transformant of AD 1-9 was cultured for 24 hours under shaking. Thereafter, $A_{600}$ was measured. As a control, DMSO and LY294002 were subjected to the same screening. Three independent tests were repeatedly performed to calculate the average value of $A_{600}$. After arranging the obtained values from the highest to the lowest, the compounds at the top group were selected as compounds for recovery from the cell proliferation disorder caused by p110α.

At the compound concentration of 0.5 µM, no compound was observed with $A_{600}$ value higher than DMSO. At the concentration of 5 µM, several compounds were observed to have the recovery from the cell proliferation disorder at a similar level to LY294002. In Table 1, ID in the library, compound name, and $A_{600}$ value of each compound are shown.

TABLE 1

Results of screening compound library

| ID | Compound | A600 |
|---|---|---|
| LY294002 | LY294002 | 0.482 |
| 2-1G | SP-3 | 0.464 |
| 2-1F | SP-2 | 0.457 |
| 3-8B | FK-A5 | 0.449 |

TABLE 1-continued

Results of screening compound library

| ID | Compound | A600 |
|---|---|---|
| 2-1E | SP-1 | 0.412 |
| 2-1H | FK228 | 0.385 |
| 2-2C | FK-A3 | 0.380 |
| 2-2A | FK-A1 | 0.364 |
| 1-11B | * | 0.363 |
| 1-2A | * | 0.355 |
| 1-1C | * | 0.351 |
| 3-3A | * | 0.350 |
| 1-11C | * | 0.347 |
| 1-6A | * | 0.346 |
| 1-2C | * | 0.345 |
| 1-1A | DMSO | 0.298 |

* Compound which is not yet open to public

All of the top listed compounds that showed a high $A_{600}$ value in the transformants with p110α expressed therein are FK228 or its analogs.

Structural formulae and 50% inhibition concentrations ($IC_{50}$) for HDAC1 and HDAC6, which were evaluated by Screening committee of anticancer drugs supported by grant-in-aid for scientific research on priority area "Cancer" from Ministry of Education, Culture, Sports, Science, and Technology, Japan, are presented in Table 2 for FK228 and its analogs suggested to have a possibility of having the PI3K inhibitory activity according to the present screening.

TABLE 2

Structural formulae and 50% inhibition concentrations ($IC_{50}$) for HDAC1 and HDAC6 of FK228 and its analogs

| Compound | Structural formula | HDAC1 IC50 | HDAC6 IC50 |
|---|---|---|---|
| FK228 $C_{24}H_{36}N_4O_6S_2$ MW: 540.70 | | 0.0036 µM | 0.39 µM |
| SP-1 (spiruchostatin A) $C_{20}H_{31}N_3O_6S_2$ MW: 473.61 | | 0.0033 µM | 1.6 µM |

TABLE 2-continued

Structural formulae and 50% inhibition concentrations (IC$_{50}$) for HDAC1 and HDAC6 of FK228 and its analogs

| Compound | Structural formula | HDAC1 IC50 | HDAC6 IC50 |
| --- | --- | --- | --- |
| SP-2 (spiruchastatin B) C$_{21}$H$_{33}$N$_3$O$_5$S$_2$ MW: 487.63 | | 0.0022 μM | 1.4 μM |
| SP-3 (5″-epi-spiruchostatin B) C$_{21}$H$_{33}$N$_3$O$_6$S$_2$ MW: 487.63 | | 0.0024 μM | 3.9 μM |
| SP-5 (spiruchostatin D) C$_{22}$H$_{35}$N$_3$O$_6$S$_2$ MW: 501.66 | | Not evaluated | Not evaluated |
| FK-A1 C$_{21}$H$_{30}$N$_4$O$_5$S$_2$ MW: 498.62 | | 0.0078 μM | 3.2 μM |

TABLE 2-continued

Structural formulae and 50% inhibition concentrations (IC$_{50}$) for HDAC1 and HDAC6 of FK228 and its analogs

| Compound | Structural formula | HDAC1 IC50 | HDAC6 IC50 |
|---|---|---|---|
| FK-A2 C$_{19}$H$_{26}$N$_4$O$_6$S$_2$ MW: 472.58 | | 0.045 μM | 4.8 μM |
| FK-A3 C$_{20}$H$_{30}$N$_4$O$_6$S$_2$ MW: 486.61 | | 0.0042 μM | 3.2 μM |
| FK-A4 C$_{20}$H$_{30}$N$_4$O$_5$S$_2$ MW: 486.61 | | 0.34 μM | 2.1 μM |

TABLE 2-continued

Structural formulae and 50% inhibition concentrations (IC$_{50}$) for HDAC1 and HDAC6 of FK228 and its analogs

| Compound | Structural formula | HDAC1 IC50 | HDAC6 IC50 |
|---|---|---|---|
| FK-A5<br>$C_{26}H_{34}N_4O_6S_2$<br>MW: 562.70 | | 0.0025 μM | 1.6 μM |
| FK-A6<br>$C_{26}H_{34}N_4O_6S_2$<br>MW: 562.70 | | 0.019 μM | 2.9 μM |

It is considered that the ratio of IC$_{50}$ for HDAC1 and HDAC6 is related to a risk of having an influence on the heart. In this regard, it is expected that any analog is considered to have a lower risk than FK228.

2. Synthesis of Depsipeptide Compounds

All of FK228 and analogs of FK228 that were used for the following tests were synthesized according to known techniques by the group headed by Prof. Tadashi Kato, one of the inventors of the present invention, of Synthetic and Medicinal Chemistry, Tohoku Pharmaceutical University. These compounds were used after being dissolved in DMSO.

Detailed synthetic pathway and synthetic method for each compound is as described in FIG. 1, and Narita et al., Chemistry—A European Journal 15, 11174-11186 (2009) (Non-Patent Document 22); Takizawa et al., Chemical Communication, 1677-1679 (2008) (Non-Patent Document 23); and Takizawa et al., Heterocycles 76, 275-290 (2008) (Non-Patent Document 24).

When explanations are given with reference to FIG. 1, first in the step (A), an aldehyde derivative having side chain R$^1$ was reacted with ethyl acetate to obtain an adduct. In the step (B), protection of the hydroxyl group and deprotection of the amino group of the adduct and ester exchange were performed in the order to produce an amino ester derivative.

In the step (C), the amino ester derivative was subjected to condensation with a carboxylic acid derivative, which had been produced from cystein, to obtain the peptide derivative (I).

In the step (D), a carboxylic acid derivative known in the literature and an amino acid ester derivative having side chain R$^2$ were condensed to each other to obtain the peptide derivative (II).

In the step (E), the two kinds of the peptide derivatives (I) and (II) obtained above were condensed to each other to obtain a tripeptide derivative. In the step (F), intramolecular lactonization, formation of disulfide bond, and deprotection of hydroxyl group were performed in the order to carry out the synthesis of the depsipeptide compound.

Meanwhile, in the step (G), a tripeptide derivative having side chain R$^1$ and side chain R$^3$, which could be produced by a pathway of related art, and the carboxylic acid derivative (II) were condensed to each other to produce a tetrapeptide derivative. In the step (H), intramolecular lactonization, formation of disulfide bond, and deprotection of hydroxyl group were performed in the order to complete synthesis of the depsipeptide compound.

3. In Vitro Evaluation of FK228 and its Analogs Regarding PI3K Inhibitory Activity A total of eleven kinds of the compounds, namely, FK228, SP-1, SP-2, SP-3, FK-A1, FK-A2, FK-A3, FK-A4, FK-A5, FK-A6, and SP-5, were subjected to an evaluation of the PI3K inhibitory activity at the concentration of 20 µM.

The PI3K (p110α/p85α) inhibitory activity was evaluated at Carna Biosciences, Inc. (Kobe) by mobility shift assay which included isolation and quantification of a substrate and the phosphorylated substrate based on the mobility in a capillary (https://www.carnabio.com/japanese/product/search.cgi?mode=profiling). Each compound was mixed with 21 nM PI3K, 1000 nM phosphatidyl inositol, 50 µM ATP, and 5 mM $MgCl_2$ in an assay buffer (20 mM HEPES, 2 mM DTT, 25 µM sodium cholate, 75 mM NaCl, and 20 µM cantharidine). After allowing the reaction to occur for 5 hours at room temperature, the mobility shift assay was performed. The test was performed in duplicate.

Inhibition rate was calculated as follows.

As a control, the kinase reaction was evaluated as product/substrate+product calculated by the MSA (mobility shift assay), and it was set as 0% inhibition rate. The value of product/substrate+product when an agent was added thereto was calculated similarly, and the inhibition rate was calculated based on a difference from the control value.

The results are presented in FIG. 2A. Direct inhibitory activity on PI3K was observed for all compounds. Among them, SP-5, FK-A1, FK-A2, FK-A3, FK-A5, and FK-A6 exhibited higher inhibition rate than FK228, and for FK-A5 that showed the most potent inhibitory activity, the inhibition rate on PI3K activity was 66.8%.

Next, for FK-A5 with the most potent inhibitory activity and FK228 as an original compound, the 50% inhibition concentrations ($IC_{50}$) for PI3K were measured and compared to that of LY294002. The results are shown in FIGS. 2B, C, and D.

FK228 and FK-A5 inhibited the PI3K activity in a concentration dependent manner. $IC_{50}$ of LY294002, FK228, and FK-A5 was 0.7 µM, 57.1 µM, and 26.2 µM, respectively. FK228 and FK-A5 were observed to have an inhibitory activity in the range of 5 to 500 µM and 1 to 300 µM, respectively. It was also found that FK-A5 inhibited PI3K more strongly than FK228.

Meanwhile, the inhibition rate of FK228 at 10 µM in the PI3K inhibition curve was 6.5% (FIG. 2C).

Based on these results, FK228 and all the analogs were found to exhibit the PI3K inhibitory activity even though there is a difference in the inhibitory activity among the analogs.

As described above, among FK228 and its analogs, the most potent PI3K inhibitory activity was shown by FK-A5 followed by FK-A6 (FIG. 2B). FK-A5 and FK-A6 are stereoisomers and they have a characteristic structure in which a benzyl (that is, phenylmethyl) group is attached on position 7 (Table 2). There is a possibility that this characteristic may contribute to the increased inhibitory activity of FK-A5 and FK-A6 compared to FK228.

4. PI3K-FK228 Docking Simulation

All of the conventional PI3K inhibitors were known to bind to an ATP binding site of p110 catalytic subunit (Non-Patent Document 27: Walker et al., Molecular Cell 6, 909-919 (2000)). Whether or not FK228 also binds to the ATP binding site was investigated.

Docking simulation was performed by using "eHiTS" (trade name, Simulated Biomolecular Systems) as a simulation software and the crystal structure data of PI3K (p110αH1047R/p85α)-wortmannin complex (Protein Data Bank Identification Code: 3HHM) as a stereo structure of PI3K as a template. When introduced to a cell, FK228 is known to undergo a disulfide bond breakage due to intracellular reducing action, and the resulting thiol group is coordinated to zinc at the active center of HDAC to exhibit an HDAC inhibitory action (Non-Patent Document 12: Furumai et al., Cancer Res 62, 4916 (2002)). As such, FK228 is presumed to be in a reduced form even for a case in which it inhibits PI3K in a cell, and thus FK228 structure in the reduced form was used for the docking model with PI3K. Regarding the docking model, the one showing the highest score under software validity evaluation of the structure was employed among the candidate models.

As a result, it was speculated that FK228 in the reduced form was deeply inserted to the ATP binding site of p110α and the binding is achieved with thiol or isopropyl deeply inserted into a pocket.

That was confirmed by determining the PI3K inhibitory activity of FK228 under various ATP concentration conditions (50 µM and 500 µM) in the experiment described in the above section 3. The results are shown in FIG. 2E. The PI3K inhibitory activity of FK228 was lowered in the presence of ATP at a high concentration. IC50 values at a standard ATP concentration (50 µM) or a high ATP concentration (500 µM) were 57.2 µM and 125.0 µM, respectively. These results suggest that FK228 is an ATP competitive PI3K inhibitor, in other words, it binds to the ATP binding site.

5. Evaluation of AKT Pathway Inhibition Based on Western Blotting

By using PC3 (prostate cancer) cells in which PTEN is deleted and AKT downstream of PI3K is constantly activated (Non-Patent Document 28: Grunwald et al., Cancer Res 62, 6141 (2002)), inhibition of AKT phosphorylation by FK228 and FK-A5 was evaluated.

PC3 cells were obtained from Cell Resource Center for Medical Research of Institute of Development, Aging, and Cancer, Tohoku University. The cells were cultured at 37° C. in the presence of 5% $CO_2$ by using RPMI1640 medium containing inactivated fetal bovine serum at the concentration of 10%.

Western blotting was performed as follows. Various kinds of the cells treated with each compound were collected and lysed in a lysis buffer (500 mM Tris-HCl pH 7.5, 100 mM NaCl, 2 mM EDTA, 1 mM sodium orthovanadate, 1% NP-40, and 1% protease inhibitor cocktail, manufactured by SIGMA-ALDRICH). After centrifugation, the supernatants were collected. The samples were subjected to 12.5% polyacrylamide gel electrophoresis and transferred on a PVDF membrane (Immobilon-FL, Millipore).

The followings were used as primary antibodies. Anti-AKT antibody ("total AKT" or "AKT"), anti-phosphorylated AKT (Ser-473) antibody ("p-AKT (S473)"), anti-phosphorylated AKT (Thr-308) antibody ("p-AKT (T308)"), anti-phosphorylated GSK-3β (Ser-9) antibody ("p-GSK-3β"), anti-phosphorylated mTOR (Ser-2448) antibody ("p-mTOR"), anti-phosphorylated p70S6K (Thr-389) antibody ("p-p70S6K"), anti-phosphorylated 4E-BP1 (Thr-37/46) antibody ("p-4EBP1"), anti-phosphorylated MEK1/2 (Ser-217/221) antibody ("p-MEK1/2"), anti-phosphorylated ERK1/2 (Thr-202/Tyr-204) antibody ("p-ERK1/2") (all of them are polyclonal antibodies, Cell Signaling Technology), and anti β-actin monoclonal antibody (Sigma Aldrich).

As a secondary antibody, "Alexa Fluor680IgG" (trade name, manufactured by Invitrogen) was used. By using "Odyssey Infrared Imaging System" (trade name, manufactured by LI-COR), expression of the protein of interest was determined.

After applying the compound first, a change in phosphorylated AKT over time was followed. The results are shown in panel A of FIG. 3.

Similarly to LY294002, both FK228 and FK-A5 lowered the expression level of phosphorylated AKT (Ser-473, Thr-308) within a short time of 5 minutes to 180 minutes without changing the expression level of the total AKT.

Next, changes in phosphorylation of AKT and downstream molecules of the AKT pathway in accordance with concentration change of FK228 and FK-A5 were examined. The application time of the compounds was 180 minutes. The results are shown in panel 13 of FIG. 3.

Both FK228 and FK-A5 inhibited in a concentration dependent manner the expression levels of phosphorylated AKT (Ser-473, Thr-308) and its downstream of the signal transduction pathway, i.e., phosphorylated GSK-3β (Ser-9), phosphorylated mTOR (Ser-2448), phosphorylated p70S6K (Thr-389), and phosphorylated 4E-BP1 (Thr-37/46). Further, while phosphorylated MEK1/2 of the RAS-MAP pathway was not inhibited, phosphorylated ERK1/2 was slightly inhibited.

Further, according to the results, the expression levels of phosphorylated AKT (S473) and (T308) was lowered by 66% and 86%, respectively, at the concentration of 10 µM, as compared to the control. It indicates the possibility that the data shown in FIG. 2A have been underestimated. Specifically, although a reducing agent was contained in the in vitro system for evaluating the PI3K inhibitory activity, there may be a possibility that it was lower than the intracellular reducing ability and the proportion of the reduced form of active FK228 was low.

Based on the above, it was shown that FK228 and FK-A5 inhibited the AKT pathway by inhibiting PI3K. Further, based on the fact that phosphorylated ERK1/2 was inhibited, it was suggested that those compounds might have an inhibitory activity for other kinase(s) in addition to PI3K or inhibit ERK1/2 via the action of other protein.

6. Evaluation of Cytotoxic Effect of FK228 and FK-A5

FK228 is a potent HDAC inhibitor having $IC_{50}$ of 1.6 to 3.6 nM against HDAC1 (Non-Patent Document 12: Fururnai et al., Cancer Res 62, 4916 (2002); and Non-Patent Document 22: Narita et al., Chemistry—A European Journal 15, 11174-11186 (2009)), and it is shown to exhibit 50% growth inhibition in a nM range against many human cancer cell lines. Based on the results so far, FK228 and FK-A5 exhibit the PI3K inhibitory activity in a µM range. Thus, the cytotoxic effect of FK228 and FK-A5 was determined by using cells which were resistant to HDAC inhibitors.

The human culture cells used were colon cancer cell lines (HCT116, CO115, and RKO). HCT116 and RKO were obtained from American Type Culture Collection (ATCC). CO115 was obtained from John M. Mariadason (Ludwig Institute for Cancer Research, Melbourne, Australia). The cells were cultured at 37° C. in the presence of 5% $CO_2$ by using RPMI1640 medium containing inactivated fetal bovine serum at the concentration of 10%.

All of HCT116, RKO, and CO115 are microsatellite instability (MSI)—positive cells. HCT116 is sensitive to an HDAC inhibitor, while RKO and CO115 have resistance to an HDAC inhibitor. With regard to RKO and CO115, it is reported that, as a result of a frame shift mutation occurred in $A_9$ (nine repeated adenines) sequence present in exon 1 of both of the HDAC2 alleles, HDAC2 protein is deficient and the loss of function of HDAC2 results in an increase in the expression level of apoptotic protease-activating factor 1 (APAF 1), thereby yielding an occurrence of abnormal control of apoptosis, and thus the cells are resistant to TSA and SAHA, which are HDAC inhibitors (Non-Patent Document 29: Ropero et al., Nature 200, 6; and Non-Patent Document 30: Hanigan et al., Gastroenterology 135, 1654-1664. e1652 (2008)). Accordingly, the expression levels of HDAC in those sells were first confirmed by Western blotting.

Western blotting was performed basically in the same manner as above except that anti-HDAC2 monoclonal antibody (Cell Signaling Technology) ("HDAC2") or anti-HDAC1 polyclonal antibody (Santa Cruz) ("HDAC1") was used as a primary antibody.

The results are shown in FIG. 4A. Unlike the previous report, weak expression of HDAC2 was also observed in RKO and CO115. With regard to RKO, there has been a report indicating a variation in the HDAC2 expression (Non-Patent Document 31: Ree et al., Nature Genetics 40, 812-813 (2008)). HDAC1 expression was observed in any cell line, but the expression level was slightly low in CO115.

Next, the cytotoxic effect was determined by MTT assay using HCT116, RKO, and CO115 cells.

Various cells were plated on a 96-well plate at the density of $8 \times 10^3$ cells/well. After pre-incubation of 24 hours, the medium was replaced with a medium containing LY294002 (50 µM), SAHA (purchased from Cayman Chemical Company; 2.5 µM), a combination of LY294002 (50 µM) and SAHA (2.5 µM), FK228 or FK-A5 (5 nM, 50 nM, 500 nM, 5 µM or 50 µM for each), or a combination of FK228 or FK-A5 (5 nM, 50 nM, or 500 nM for each) and LY294002 (50 µM), and the cells were cultured further.

After 24 hours, the number of live cells was determined by using "Cell counting kit-8" (trade name, manufactured by DOJINDO CO., LTD). The kit uses water soluble tetrazolium salt WST-8 as a color developing agent and WST-8 produces formazan by an action of intracellular dehydrogenase. The amount of formazan dye and the number of live cells are in proportional relationship, and by measuring the absorbance of formazan at 450 nm using a microplate reader (trade name: "SpectraMax M2e", manufactured by Molecular Devices), the number of live cells was counted.

The results are shown in FIGS. 4B, C, and D.

In HCT116 cells that are sensitive to an HDAC inhibitor, about 50% (43 to 70%) cell death was caused by SAHA or a low concentration (at the level of 5 nM to 500 nM or so) of FK228 or FK-A5. On the other hand, although weak expression of HDAC2 was observed, RKO and CO115 cells were resistant to SAHA and FK228 or FK-A5 up to 50 nM or so (6 to 15% cell death). With regard to LY294002, all cells were sensitive (50 to 60% cell death). With regard to the combined use of SAHA and LY294002, an enhanced cytotoxic effect (that is, additive effect) was observed in HCT116 and RKO, but no such enhancement was observed for CO115.

In all types of cells, both FK228 and FK-A5 at a high concentration (at µM levels), at which the PI3K inhibitory activity was exhibited, very significantly reduced the number of cells.

Further, with regard to the combined use of a low concentration of FK228 or FK-A5 and LY294002, a synergistic effect was observed for RKO and CO115 cells, but the cytotoxic effect was lower than that of FK228 or FK-A5 alone at a high concentration (5 µM) (FIG. 4B).

Based on the results, a possibility was suggested that FK228 and FK-A5 at a high concentration (at µM level) exhibited a very potent cytotoxic effect even for the cells with resistance to an HDAC inhibitor and the PI3K inhibitory activity exhibited at a high concentration enhanced the cytotoxic effect.

7. Analysis of Cell Death Caused by FK228 and FK-A5 and Evaluation of Apoptosis Induction To analyze the cell death caused by administration of FK228 and FK-A5, as a cell cycle analysis, FACS analysis (fluorescence-activated cell sorting analysis) was performed first.

HCT116 cells were plated on a six-well plate at 2×10$^5$ cells/well, and after pre-incubation for 24 hours, the cells were cultured further for 24 hours in the presence of each agent, i.e., SAHA, LY294002, FK228, and/or FK-A5 to the cells in the same conditions as those described in the above section 6. The cells were collected, fixed with ethanol, stained with iodopropidium/PBS solution, and analyzed by using "Cytomics FC500 Flow Cytometry System" (trade name, manufactured by Beckman Coulter). The cell cycle fractions were calculated by using "Multicycle software" (trade name, manufactured by Phenomix Flow Systems).

The results are shown in FIGS. 5A, 5B, and 5C. An HDAC inhibitor induces arrest of the cell cycle via an increased expression of $p21^{WAF1}$ (Non-Patent Document 32: Xu et al., Oncogene 26, 5541-5552 (2007)), and there are various reports regarding which one of G1/S phase and G2/M phase is predominantly arrested depending on the concentrations of HDAC inhibitors or differences in cell types (Non-Patent Document 33: Richon et al., Proc. Natl. Acad. Sci. 97, 10014 (2000); Non-Patent Document 34: Nakajima et al., Exp. Cell Res. 241, 126-133 (1998); and Non-Patent Document 35: Kumagai et al., Int. J. of Cancer 121, 656-665 (2007)).

In the present experiment, SAHA induced arrest of G2/M phase, which was prominent in HCT116 cells. Similarly to SAHA, FK228 and FK-A5 at a low concentration also induced cell cycle arrest, predominantly at G2/M phase (FIGS. 5A to 5C).

Meanwhile, it is shown that LY294002 causes arrest of G0/G1 phase and induces apoptosis weakly. Also in this experiment, LY294002 induced arrest of G0/G1 phase in HCT116 cells (FIGS. 5A to 5C). With regard to the combined use of SAHA and LY294002 and the combined use of FK228 or FK-A5 at a low concentration and LY294002, the subG1 fractions were significantly increased to 20 to 40%, indicating strong induction of apoptosis (FIGS. 5A to 5C).

On the other hand, FK228 or FK-A5 at a high concentration (5 µM) alone induced strong apoptosis (36 to 37% of subG1 fraction), and the DNA histogram showed a similar result to those of the combined use of SAHA and LY294002 and the combined use of FK228 or FK-A5 at a low concentration and LY294002 (FIGS. 5A and 5B). With regard to the cell cycle fraction analysis, FK-A5 at a high concentration was similar to SAHA or the combined use of FK-A5 at a low concentration and LY294002 (FIG. 5C).

From the above, it was shown that the influence of FK228 and FK-A5 at a high concentration (at µM level) on the cell cycle and apoptosis induced therefrom were similar to those of a case in which an HDAC inhibitor and a PI3K inhibitor were used in combination.

In order to further confirm that the cell death caused by FK228 is due to the induction of apoptosis, Western blotting was performed basically in the same manner as above, except that samples treated with SAHA (2.5 µM) or FK228 at concentrations described in the drawing were used and that, as primary antibodies, anti-pARP-1/2 polyclonal antibody (Santa Cruz) ("PARP"), anti-phosphorylated (p)AKT antibody (S473) (Cell signaling) ("pAKTS473"), anti-AKT antibody ("total AKT"), anti-acetylated histone H3 antibody (Upstate) ("Acetylated H3"), and anti-acetylated histone H4 antibody (Upstate) ("Acetylated H4") were used. With regard to Western blotting, HCT116 cells were treated for 24 hours with SAHA or FK-228 at predetermined concentrations, and then the expression of PARP, cleaved PARP, phosphorylated AKT (S473), AKT, acetylated histone H3, and acetylated histone H4 was analyzed.

The results are shown in FIG. 5D. Induction of apoptosis by FK228 was supported by the increase in Cleaved PARP in HCT116 cells. Like the results obtained from FCAS analysis, Cleaved PARP was increased most with the high concentration of FK228 (5 µM) and also strong induction of apoptosis was shown. Further, it was also found that, at the same time, the high concentration of FK228 (5 µM) inhibited the phosphorylated AKT and enhanced the expression of acetylated histone.

From the above, it was shown that a high concentration of FK228 or FK-A5 (at µM level) can strongly induced apoptosis, and at that time, it exhibited an activity of double inhibitor of HDAC and PI3K.

8. Synthesis of Depsipeptide Compound (2)

Depsipeptide compound FK-A7 to A13 and FK-A17 were synthesized in the same manner as the above section 2 and characterized. The structural formulae and 50% inhibition concentrations ($IC_{50}$) of the compounds for PI3K (p110α/p85α), which were determined in the same manner as the above section 3, are described in Table 3, together with those for FK228, SAHA, and LY294002 for comparison. In Table 3, 50% inhibition concentrations ($IC_{50}$) of FK228 and SAHA for HDAC1 were evaluated by Screening committee of anticancer drugs supported by grant-in-aid for scientific research on priority area "Cancer" from Ministry of Education, Culture, Sports, Science, and Technology, Japan.

TABLE 3

Structural formulae and 50% inhibition concentrations (IC$_{50}$) for PI3K and HDAC1 of FK-A7 to A13 and A17

| Compound | Structural formula | PI3K IC50 | HDAC1 IC50 |
| --- | --- | --- | --- |
| FK228 | | 57.1 µM | 3.6 nM |
| FK-A5 | | 27.3 µM | 2.5 nM |
| FK-A7 | | 32.2 µM | Not evaluated |

TABLE 3-continued

Structural formulae and 50% inhibition concentrations (IC$_{50}$) for PI3K and HDAC1 of FK-A7 to A13 and A17

| Compound | Structural formula | PI3K IC50 | HDAC1 IC50 |
| --- | --- | --- | --- |
| FK-A8 | | 44.7 μM | Not evaluated |
| FK-A9 | | 14.1 μm | Not evaluated |
| FK-A10 | | 26.7 μM | Not evaluated |

TABLE 3-continued

Structural formulae and 50% inhibition concentrations (IC$_{50}$) for PI3K and HDAC1 of FK-A7 to A13 and A17

| Compound | Structural formula | PI3K IC50 | HDAC1 IC50 |
|---|---|---|---|
| FK-A11 | | 6.7 μM | Not evaluated |
| FK-A12 | | 7.2 μM | Not evaluated |
| FK-A13 | | 8.5 μM | Not evaluated |

TABLE 3-continued

Structural formulae and 50% inhibition concentrations (IC$_{50}$) for PI3K and HDAC1 of FK-A7 to A13 and A17

| Compound | Structural formula | PI3K IC50 | HDAC1 IC50 |
|---|---|---|---|
| FK-A17 | | 20.2 μM | Not evaluated |
| SAHA | | Not evaluated | 221 nM |
| LY294002 | | 0.7 μM | Not evaluated |

9. Evaluation of AKT Pathway Inhibition by FK-A11 Based on Western Blotting

Inhibition of AKT phosphorylation by FK-A11 was evaluated in the same manner as the above section 5 and it was compared to those by FK-A5 and FK228. However, the application time was 180 minutes and, as primary antibodies, anti-phosphorylated AKT (Ser-473) antibody ("p-AKT (S473)"), anti-phosphorylated AKT (Thr-308) antibody ("p-AKT (T308)"), anti-AKT antibody ("AKT"), and anti-β-actin monoclonal antibody ("B-actin") were used.

The results are shown in FIG. 6. It was shown that the inhibition of AKT phosphorylation by FK-A11 occurred at a lower concentration than FK-A5 and FK228.

10. Evaluation of Cytotoxic Effect by FK-A11

The cytotoxic effect of FK-A11 was examined by MTT assay in the same manner as the above section 6. However, the human culture cells used were colon cancer (HCT116, CO115, and RKO) cell lines and a non-cancerous fibroblast cell line, KMST6, as normal cells, and FK-A11 was used at 5 nM, 50 nM, 500 nM, 5 μM, or 50 μM.

The results are shown in FIGS. 7A to 7D.

In HCT116 and RKO cells, a significant cell death was caused by FK-A11 at a low concentration (that is, at the level of 5 nM to 500 nM or so). On the other hand, HDAC inhibitor-resistant CO115 cells were resistant to FK-A11 up to 50 nM or so, but it caused strong cell death from 500 nM at which the PI3K inhibitory activity was presumed to be exhibited. Meanwhile, at such a concentration, the non-cancerous KMST6 cells did not show any significant cell death.

Comparison of the results from FK228, FK-A5 and FK-A11 is shown in FIGS. 8A to 8C.

Based on these results, it was demonstrated that FK-A11 having a very potent inhibitory activity on p110α exhibited more potent inhibitory effect on cell proliferation of all cancer cell lines than that of FK228 or FK-A5.

The present application is based on Japanese Patent Application No. 2011-217378 filed Sep. 30, 2011 and those described in Description and Claims of Japanese Patent Application No. 2011-217378 are incorporated herein in its entirety.

The invention claimed is:

1. A pharmaceutical composition for treatment of refractory cancer comprising a phosphatidylinositol-3-kinase (PI3K) inhibitor as an effective component, wherein the PI3K inhibitor is a depsipeptide compound having a formula selected from the group consisting of the following formulae 5 to 12 and 14 to 20, and a physiologically acceptable salt thereof:
Formula 5
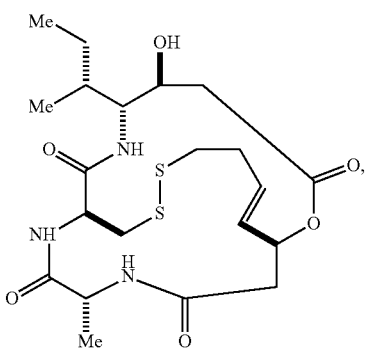
Formula 6
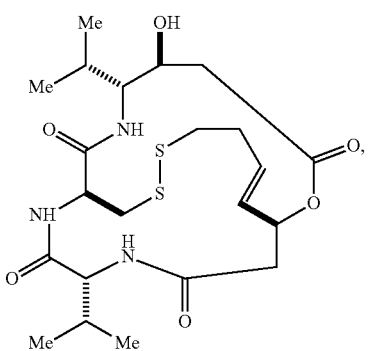
Formula 7
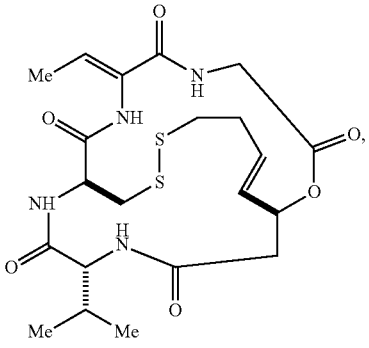
Formula 8
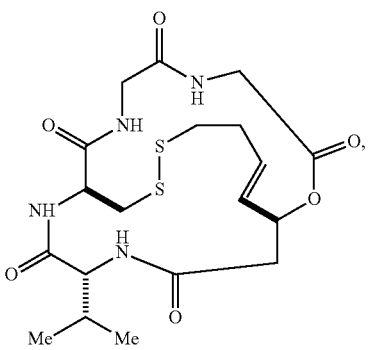
-continued
Formula 9
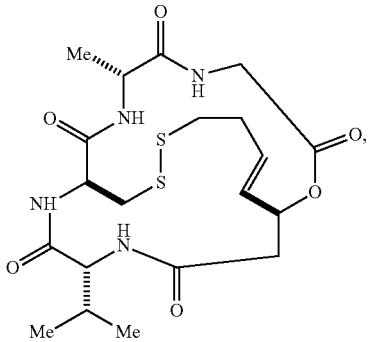
Formula 10
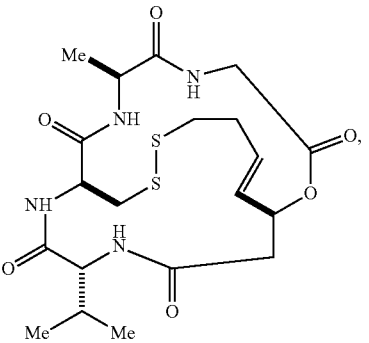
Formula 11
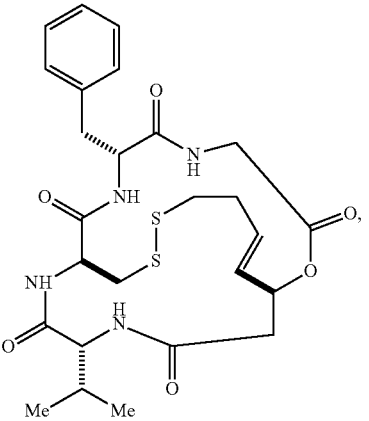
Formula 12
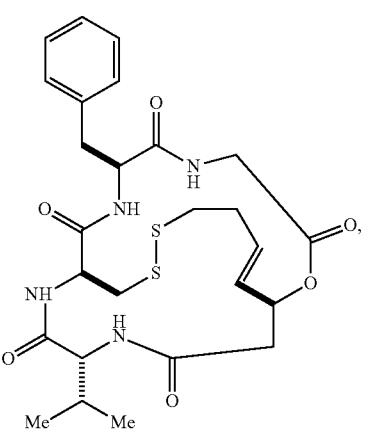

-continued
Formula 14
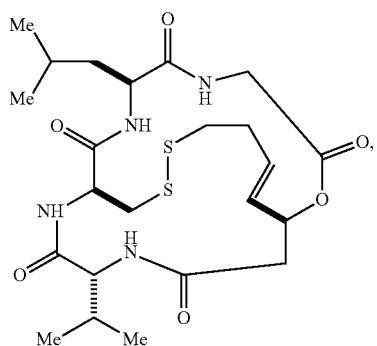
Formula 15
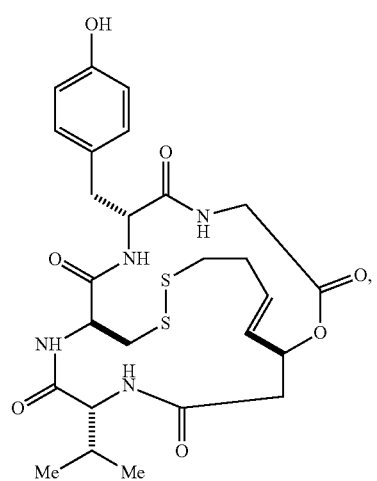
Formula 16
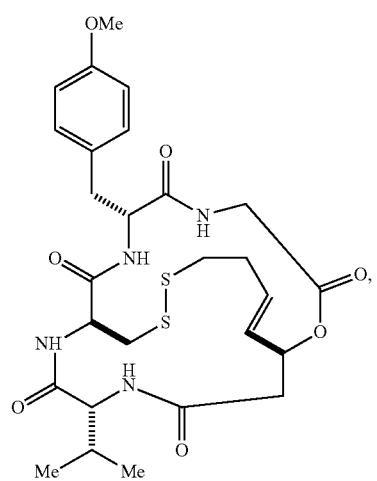
-continued
Formula 17
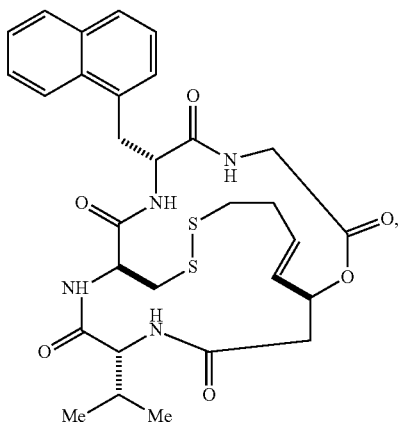
Formula 18
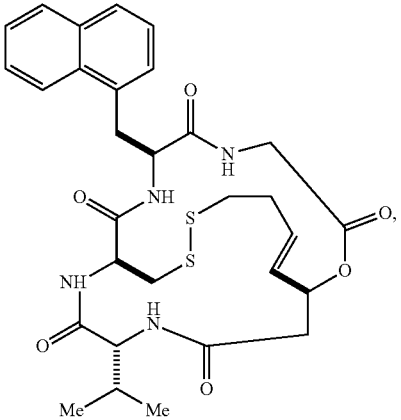
Formula 19
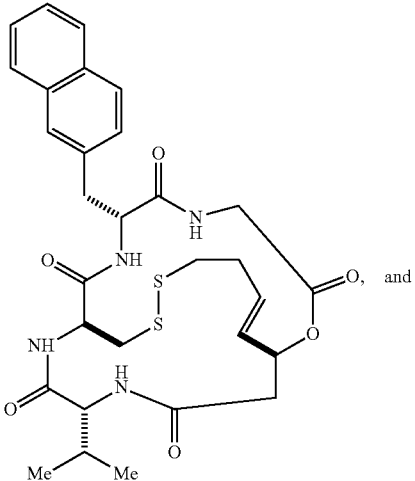
and -continued Formula 20

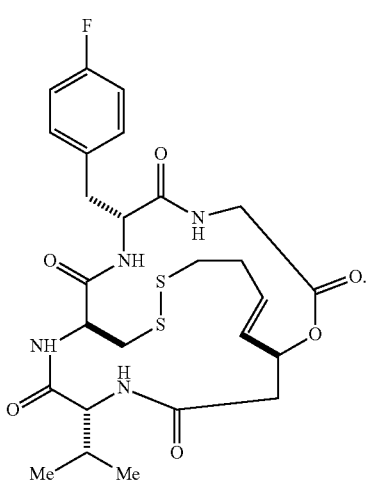

2. A depsipeptide compound represented by the following formula 1:

Formula 1

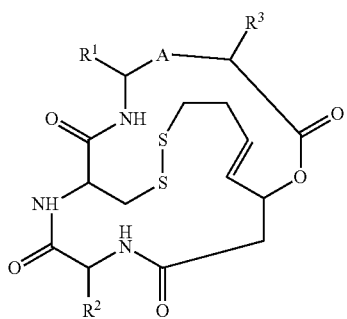

wherein A is —CONH—, $R^1$ is naphthyl alkyl group, and $R^2$ and $R^3$ may be the same or different from each other and each represents a hydrogen atom, a lower alkyl group, a lower alkylidene group, a substituted or unsubstituted aryl group, or a substituted or unsubstituted aralkyl group, wherein the lower alkyl group is a linear or branched alkyl group having 1 to 6 carbon atoms and the lower alkylidene group is a linear or branched alkylidene group having 1 to 6 carbon atoms; or a physiologically acceptable salt thereof.

3. The depsipeptide compound or the physiologically acceptable salt thereof according to claim 2, wherein $R^1$ in the formula 1 is naphthyl methyl group.

4. A pharmaceutical composition for treatment of refractory cancer, comprising as an effective component, the depsipeptide compound or a physiologically acceptable salt thereof according to claim 2.

5. A method for treating refractory colon or prostate cancer by inhibiting phosphatidylinositol-3-kinase (PI3K), comprising: administering to a subject in need thereof the pharmaceutical composition according to claim 1.

6. A method for treating refractory colon or prostate cancer by inhibiting phosphatidylinositol-3-kinase (PI3K), comprising: administering to a subject in need thereof the depsipeptide compound or the physiologically acceptable salt thereof according to claim 2.

* * * * *